(12) United States Patent
Phan et al.

(10) Patent No.: US 8,632,532 B2
(45) Date of Patent: Jan. 21, 2014

(54) CATHETER WITH TISSUE PROTECTING ASSEMBLY

(75) Inventors: Huy D. Phan, San Jose, CA (US); David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/551,450

(22) Filed: Jul. 17, 2012

(65) Prior Publication Data
US 2012/0283719 A1 Nov. 8, 2012

Related U.S. Application Data

(63) Continuation of application No. 12/499,650, filed on Jul. 8, 2009, now Pat. No. 8,221,407, which is a continuation of application No. 10/660,820, filed on Sep. 12, 2003, now Pat. No. 7,569,052.

(51) Int. Cl.
*A61B 18/14* (2006.01)
*A61B 18/18* (2006.01)

(52) U.S. Cl.
USPC .................................. 606/33; 606/41

(58) Field of Classification Search
USPC .................................. 606/27–52
See application file for complete search history.

(56) References Cited

U.S. PATENT DOCUMENTS

| | | |
|---|---|---|
| 4,709,698 A | 12/1987 | Johnston et al. |
| 4,913,164 A | 4/1990 | Greene et al. |
| 5,100,388 A | 3/1992 | Behl et al. |
| 5,237,996 A | 8/1993 | Waldman et al. |
| 5,254,088 A | 10/1993 | Lundquist et al. |
| 5,441,483 A | 8/1995 | Avitall |
| 5,492,119 A | 2/1996 | Abrams |
| 5,582,609 A | 12/1996 | Swanson et al. |
| 5,800,432 A | 9/1998 | Swanson |
| 5,846,239 A * | 12/1998 | Swanson et al. ............... 606/41 |
| 5,860,974 A | 1/1999 | Abele |
| 5,876,369 A * | 3/1999 | Houser ........................ 604/22 |
| 5,885,277 A | 3/1999 | Korth |
| 5,891,134 A | 4/1999 | Goble et al. |
| 5,925,038 A | 7/1999 | Panescu et al. |
| 6,014,589 A | 1/2000 | Farley et al. |
| 6,142,994 A | 11/2000 | Swanson et al. |
| 6,161,047 A | 12/2000 | King et al. |
| 6,238,389 B1 | 5/2001 | Paddock et al. |
| 6,330,473 B1 | 12/2001 | Swanson et al. |
| 6,352,534 B1 | 3/2002 | Paddock et al. |
| 6,405,067 B1 | 6/2002 | Mest et al. |
| 6,454,766 B1 | 9/2002 | Swanson et al. |
| 6,475,213 B1 | 11/2002 | Whayne et al. |
| 6,482,203 B2 | 11/2002 | Paddock et al. |
| 6,485,455 B1 | 11/2002 | Thompson et al. |

(Continued)

*Primary Examiner* — Linda Dvorak
*Assistant Examiner* — Amanda Scott
(74) *Attorney, Agent, or Firm* — Seager, Tufte & Wickhem, LLC

(57) ABSTRACT

A medical probe includes an elongate member having a proximal end and a distal end, an ablative element mounted to the distal end of the elongate member, and a cage assembly mounted to the distal end of the elongate member, the cage assembly at least partially covers the ablative element. A method of treating tissue in a body includes inserting an ablative element in the body, placing the ablative element adjacent the tissue, and maintaining a distance between the ablative element and the tissue using a protective catheter element that circumscribes at least a portion of the ablative element.

22 Claims, 19 Drawing Sheets

(56) References Cited

U.S. PATENT DOCUMENTS

| | | |
|---|---|---|
| 6,529,775 B2 | 3/2003 | Whitebook et al. |
| 6,582,429 B2 | 6/2003 | Krishnan et al. |
| 6,676,657 B2 | 1/2004 | Wood |
| 7,291,146 B2 * | 11/2007 | Steinke et al. .................. 606/41 |
| 2002/0128640 A1 | 9/2002 | Swanson |
| 2003/0014044 A1 | 1/2003 | Krishnan et al. |
| 2003/0028188 A1 | 2/2003 | Paddock et al. |

* cited by examiner

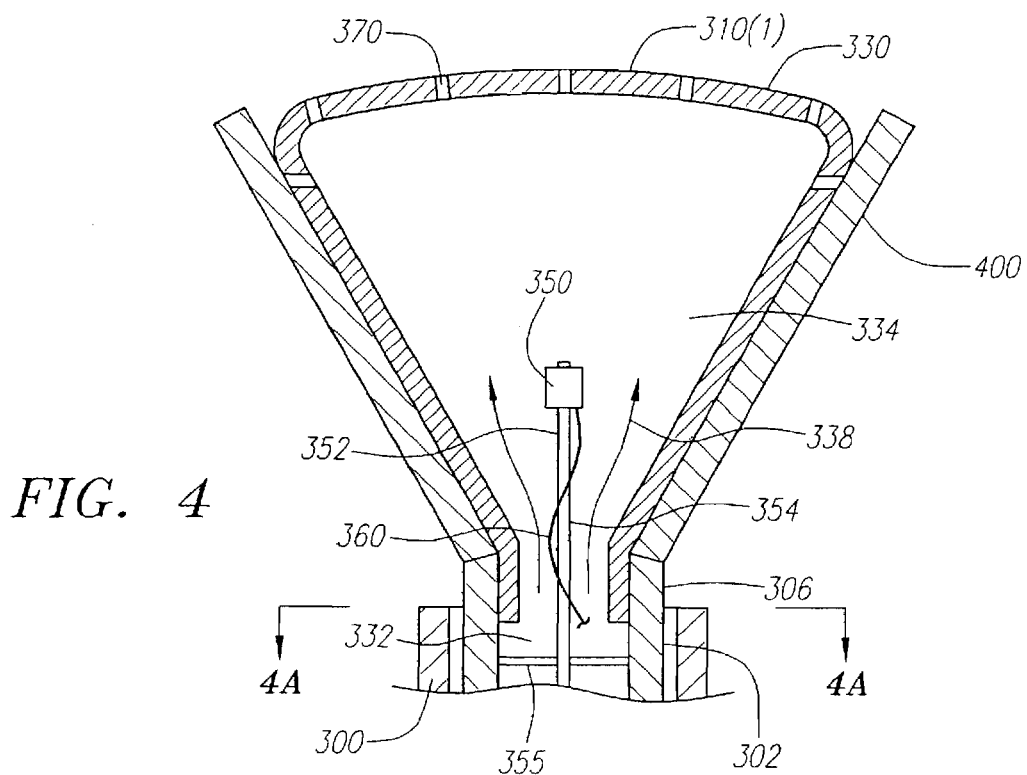
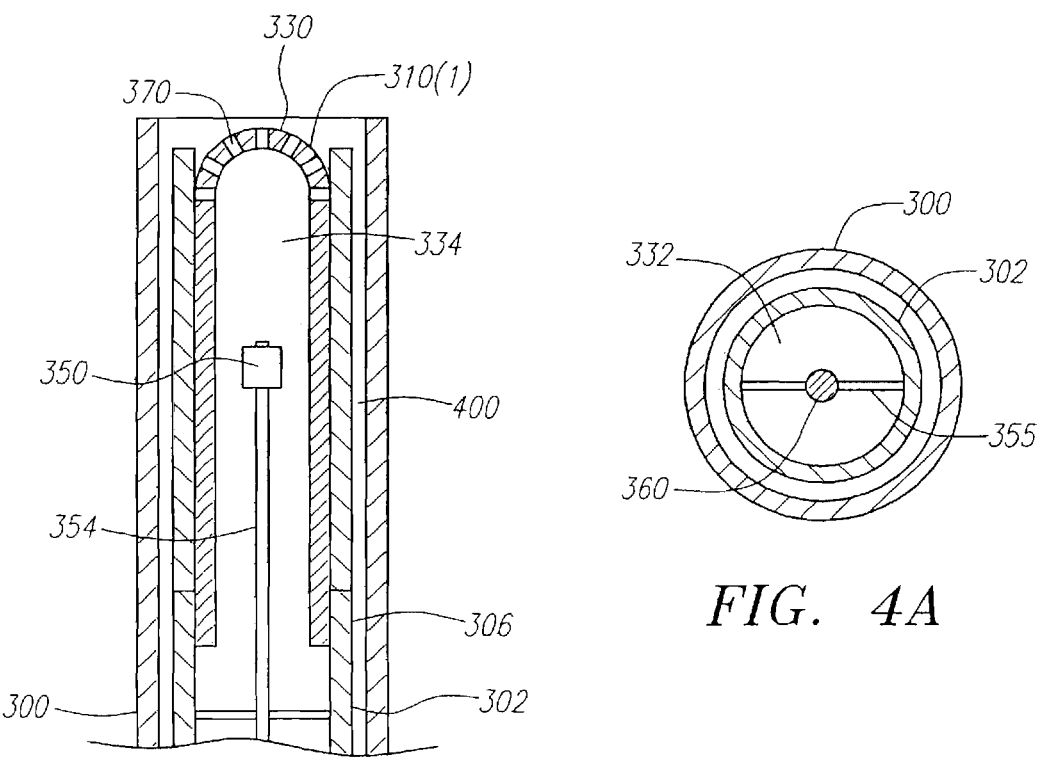

SECTION B-B

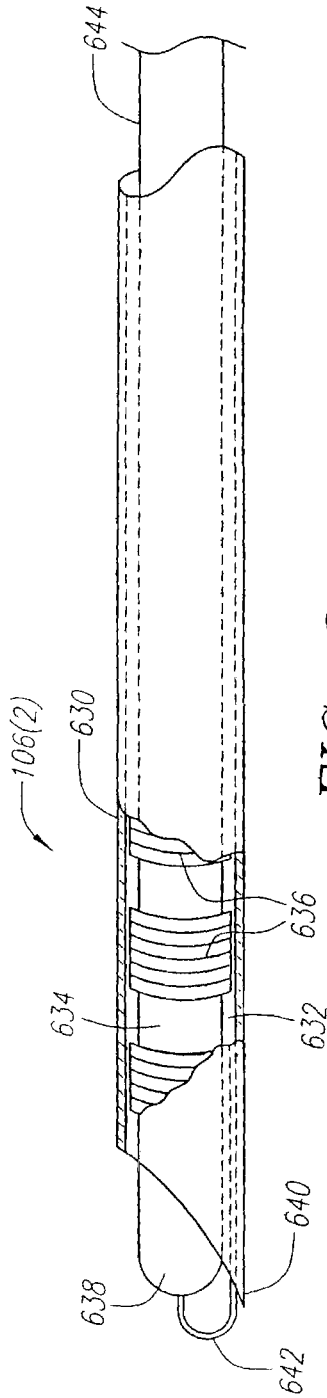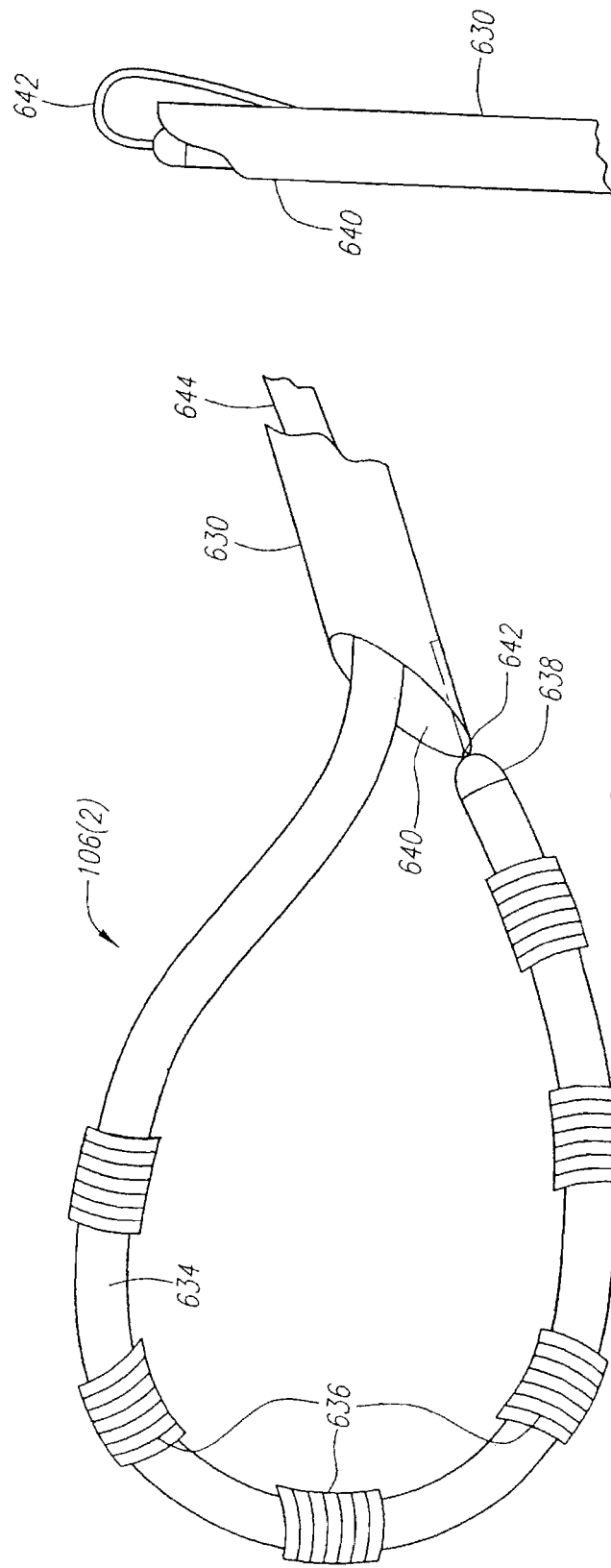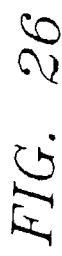

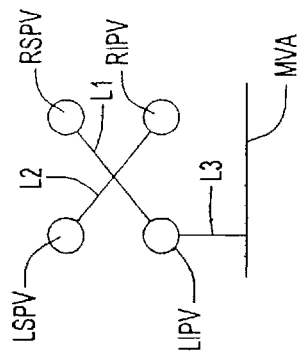
FIG. 32A
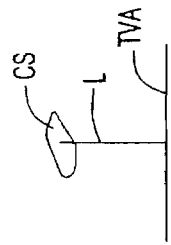
FIG. 32B
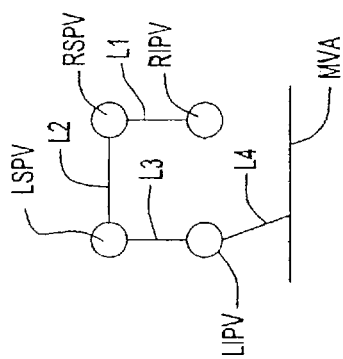
FIG. 31
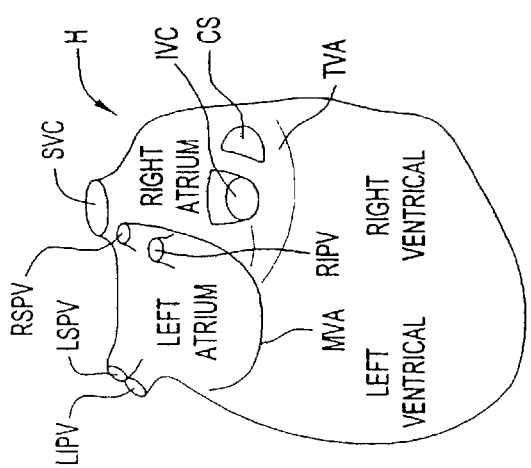
FIG. 33A
FIG. 33B
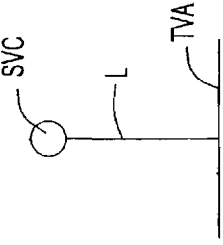
FIG. 33C

CATHETER WITH TISSUE PROTECTING ASSEMBLY

RELATED APPLICATION

This application is a continuation of U.S. application Ser. No. 12/499,650, filed Jul. 8, 2009, now U.S. Pat. No. 8,221,407, which is a continuation of U.S. application Ser. No. 10/660,820, filed Sep. 12, 2003, now U.S. Pat. No. 7,569,052; the entire disclosures of which are incorporated herein by reference.

FIELD OF THE INVENTION

The present invention pertains to devices and methods for ablation of tissue, and more particularly, to ablation devices and methods for creating lesions within internal body organs, such as the heart.

BACKGROUND

Physicians make use of catheters today in medical procedures to gain access into interior regions of the body to ablate targeted tissue areas. For example, in electrophysiological therapy, ablation is used to treat cardiac rhythm disturbances. During these procedures, a physician steers a catheter through a main vein or artery into the interior region of the heart that is to be treated. The physician places an ablating element carried on the catheter near the targeted cardiac tissue, and directs energy from the ablating element to ablate the tissue and form a lesion. Such procedure may be used to treat arrhythmia, a condition in the heart in which abnormal electrical signals are generated in the heart tissue.

In certain procedures, it may be desirable to produce a deep lesion. For example, it may be desirable to produce a transmural lesion (lesion that extends the depth of a tissue) within ventricle tissue, because shallow or incomplete lesions may otherwise allow electrical signals to travel through the non-ablated tissue beneath the lesion. Therefore, it is believed that deep or transmural lesions can more efficiently block undesirable electrical paths. Because the ventricle tissue is thick, however, it may be difficult to create transmural lesions using the current technology.

An ablation procedure using a unipolar arrangement involves placing an indifferent patch electrode or a ground pad on a patient skin. Ablation energy is directed from another electrode (the ablating electrode) placed against the target tissue, while the indifferent patch electrode is electrically coupled to a ground or return input on the radio-frequency generator, thereby completing the energy path. In this case, ablation energy will flow from the ablating electrode to the patch electrode. One of the disadvantages of this procedure is that much of the RF energy is dissipated or lost through intervening organs, tissues, and/or blood pool between the ground pad and the target tissue that is being ablated. As the result, it is more difficult to ablate tissue below the surface of the target site using current unipolar arrangements.

An ablation procedure using a bipolar arrangement involves using an ablation catheter that carries two electrodes. In this case, ablation energy will flow from one electrode (the ablating electrode) on the catheter to an adjacent electrode (the indifferent electrode) on the same catheter. Because both the ablating electrode and the indifferent electrode are usually located on one side of the tissue to be ablated, some of the ablation energy delivered by the ablating electrode may only affect tissue that is closer to the surface of the target site, and may tend to return to the indifferent electrode without substantially affecting deeper tissue. As a result, it is more difficult to ablate tissue below the surface of the target site using current bipolar arrangements.

Another problem associated with current ablation devices is that during an ablation procedure, a return electrode used for returning energy to an ablation source may heat up. In the unipolar arrangement where the return electrode is placed in contact with a patient's skin, the overheating of the return electrode may cause injury to the patient's skin. In the bipolar arrangement where the return electrode is placed within the body and adjacent to the ablating electrode, the overheating of the return electrode may cause internal healthy tissue that is in contact with the return electrode to be unnecessarily heated.

Furthermore, ablation of heart tissue poses another challenge in that the heart is constantly moving during an ablation procedure. As a result, it is difficult to maintain stable contact between an ablating or ground electrode and the constantly moving target tissue.

Thus, there is currently a need for an improved ablation device and method for creating lesions.

SUMMARY OF THE INVENTION

A medical probe includes an elongate member having a proximal end and a distal end, an ablative element mounted to the distal end of the elongate member, and a cage assembly mounted to the distal end of the elongate member. The cage assembly at least partially covers the ablative element and prevents the ablative element from directly contacting and damaging a healthy tissue due to overheating of the ablative element during use. By means of non-limiting example, the cage assembly may include a distal end, a proximal end, and a plurality of struts secured between the distal and proximal ends. The cage assembly may also be made from a woven or braided structure.

A method of treating tissue in a body includes inserting an ablative element in the body, placing the ablative element adjacent the tissue, and maintaining a distance between the ablative element and the tissue using a protective catheter element that circumscribes at least a portion of the ablative element.

Other and further aspects and features of the invention will be evident from reading the following detailed description of the drawings, which is intended to illustrate, not limit, the invention.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which:

FIG. 4 is a cross-sectional view of an embodiment of an electrode structure and stabilizer used in the ablation catheter of FIG. 3, particularly showing the electrode structure in a deployed configuration;

FIG. 5 is a cross-sectional view of the electrode structure of FIG. 4, particularly showing the electrode structure in an undeployed configuration;

FIG. 24 is a partial side view of an alternative embodiment of a ground probe that may be used with the system of FIG. 1;

FIG. 25 is a partial side view of the distal region of the ground probe of FIG. 24, showing the sleeve advanced from the sheath to form a loop;

FIG. 26 is a partial side view of an alternative embodiment of the ground probe of FIG. 24, showing the spring member secured to the exterior of the sheath;

FIG. 31 shows, in diagrammatic form, anatomic landmarks for lesion formation in left and right atriums;

FIGS. 32A and 32B show representative lesion patterns in a left atrium that may be formed using the system of FIG. 1; and FIG. 33A-33C show representative lesion patterns in a right atrium that may be formed using the system of FIG. 1.

DESCRIPTION OF THE ILLUSTRATED EMBODIMENTS

Figure 1:
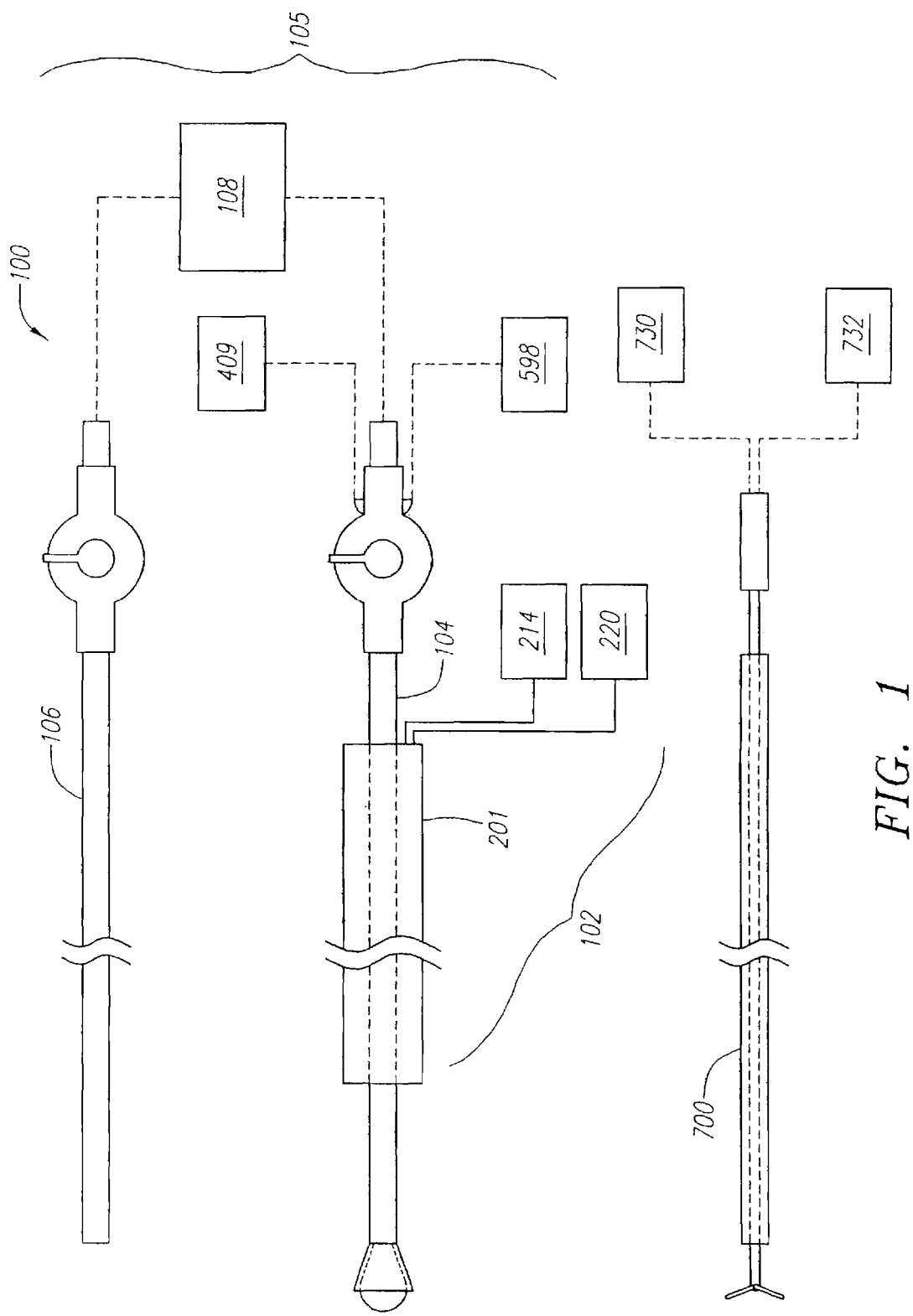
FIG. 1 is a block diagram of an ablation system constructed in accordance with one embodiment of the present invention.

Various embodiments of the present invention are described hereinafter with reference to the figures. It should be noted that the figures are not drawn to scale and that elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated.

Referring to FIG. 1, a tissue ablation system 100 constructed in accordance with one embodiment of the present invention is shown. The system 100 comprises an imaging cannula assembly 102, which includes a cannula 201, an imaging device 214 (e.g., a charge coupled device (CCD) camera) that provides imaging functionality to the cannula 201, and a light source 220 that provides optical viewing functionality to the cannula 201. The imaging cannula assembly 102 is configured to be partially inserted through a patient's skin in order to provide access to, and imaging of, a target area on the exterior surface of an organ, such as a heart.

The system 100 further comprises an ablation assembly 105, which includes an ablation catheter 104, a pump 409 for providing an inflation medium to the ablation catheter 104, a vacuum 598 that provides stabilizing functionality to the ablation catheter 104, a ground catheter 106, and an ablation source 108. The ablation catheter 104 is configured to be introduced to a target area facilitated by the cannula assembly 102, and the ground catheter 106 is configured to be intravenously introduced within an organ. The ablation catheter 104 and the ground catheter 106 are electrically coupled to the respective positive and negative terminals (not shown) of the ablation source 108, which is used for delivering ablation energy to the ablation catheter 104 to ablate target tissue during use. The ablation source 108 is preferably a radio frequency (RF) generator, such as the EPT-1000 XP generator available at EP Technologies, Inc., San Jose, Calif.

The system 100 also includes a mapping catheter 700 for sensing an electric signal at a heart and a mapping processor 730 that analyzes sensed signals or data from the catheter 700 to thereby determine a target site to be ablated, and a vacuum 732 that provides stabilizing functionality to the mapping catheter 700.

The Cannula

Figure 2A:
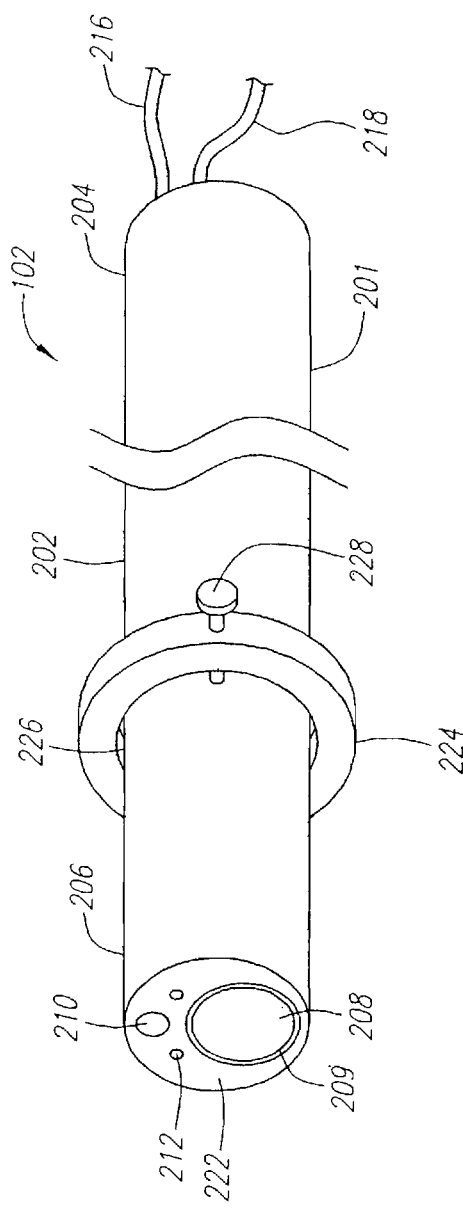
FIG. 2A is a perspective view of an embodiment of a cannula that may be used with the system of FIG. 1.
Figure 2C:
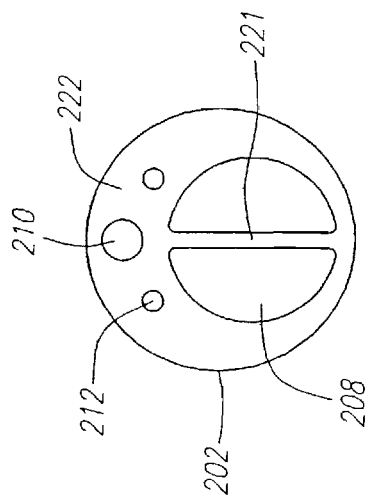
FIG. 2C is a cross-sectional view of an alternative embodiment of the cannula of FIG. 2A or 2B.
Figure 2B:
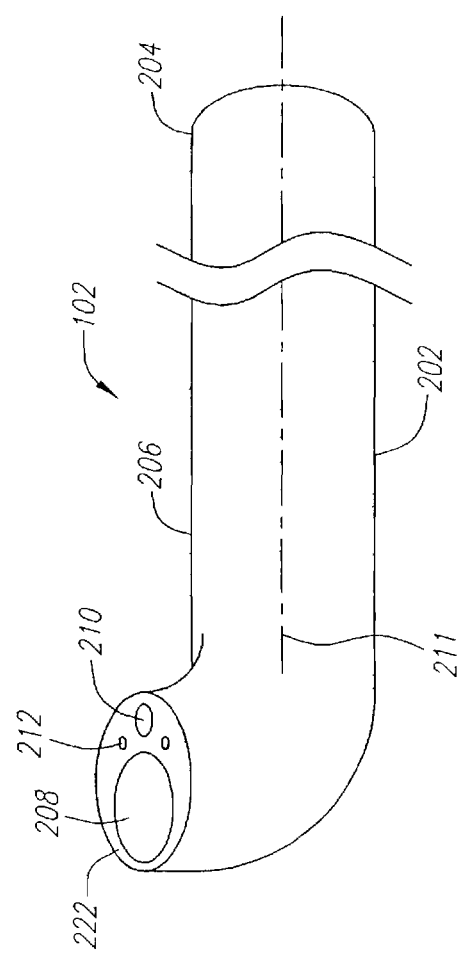
FIG. 2B is a perspective view of an alternative embodiment of a cannula that may be used with the system of FIG. 1.

Referring now to FIG. 2, the details of the cannula 201 will be described. The cannula 201 includes a shaft 202 having a proximal end 204, a distal end 206, and a lumen 208 extending between the proximal end 204 and the distal end 206. In the illustrated embodiment, the shaft 202 has a circular cross-sectional shape and a cross-sectional dimension that is between 0.25 to 1.5 inches. However, the shaft 202 may also have other cross-sectional shapes and dimensions. As shown in FIG. 2A, the distal end 206 of the shaft 202 has a substantially pre-shaped rectilinear geometry. Alternatively, the distal end 206 may have a pre-shaped curvilinear geometry (FIG. 2B), which may be used to guide the ablation catheter 104 away from a longitudinal axis 211 of the shaft 202.

The shaft 202 is made of, for example, a polymeric, electrically nonconductive material, like polyethylene, polyurethane, or PEBAX® material (polyurethane and nylon). Alternatively, the shaft 202 is made from a malleable material, such as stainless steel or aluminum, thereby allowing a physician to change the shape of the shaft 202 before or during an operation. Even more alternatively, the distal end 206 is made softer than the proximal portion of the cannula 201 by using different material and/or having a thinner wall thickness. This has the benefit of reducing the risk of injury to tissue that the distal end 206 may come in contact with during an operation. The cannula 201 also includes a liner 209 composed of a suitable low friction material, e.g., TEFLON®, Polyetheretherketone (PEEK), polyimide, nylon, polyethylene, or other lubricious polymer linings, to reduce surface friction with the ablation catheter 104 as it slides within the lumen 208.

The cannula 201 also includes an imaging window 210 located at the distal end 206 of the shaft 202, and an imaging cable 216 housed within a wall 222 of the cannula 201. The imaging cable 216 couples the imaging device 214 to the imaging window 210, so that the cannula 201 is capable of sensing images in the vicinity of the distal end 206 of the shaft 202. The cannula 201 further includes one or more optical windows 212 (in this case, two) located at the distal end 206 of the shaft 202, and fiber-optic cables 218 housed within the wall 222 of the cannula shaft 202. The fiber-optic cables 218 couple the light source 220 to the optical windows 212, so that the cannula 201 is capable of supplying light to illuminate objects that are being imaged.

The cannula 201 optionally includes a stopper 224 slidably secured to the surface of the shaft 202. The stopper 224 includes an opening 226 through which the shaft 202 can slide, and a locking mechanism 228 for securing the stopper 224 to the shaft 202 during use of the cannula 201. In the illustrated embodiment, the locking mechanism 228 includes a screw that can be screwed through a wall of the stopper 224 into engagement with the outer surface of the cannula shaft 202. In an alternative embodiment, the opening 226 of the stopper 224 can have a cross-sectional dimension equal to a cross-sectional dimension of the shaft 202 to provide a frictional engagement between the stopper 224 and the shaft 202. Other securing mechanisms may also be used. In another alternative embodiment, the stopper 224 may be fabricated together with the shaft 202 as one unit. In any event, the stopper 224 is configured for bearing against a trocar (not shown) secured to a patient's skin during an operation. Alternatively, the stopper 224 can be configured to directly bear against a patient's skin.

As shown in FIG. 2C, in another embodiment, the cannula 201 further includes one or more dividers 221 (in this case, one) for separating the lumen 208 into two or more compartments. Such configuration allows more than one device, such as a catheter, probe, scissor, clamp, and forceps, to be inserted into a patient through the cannula shaft 202, while the other compartment carries a catheter, such as the ablation catheter 106 or the mapping catheter 700.

The Ablation Catheter

Figure 3:
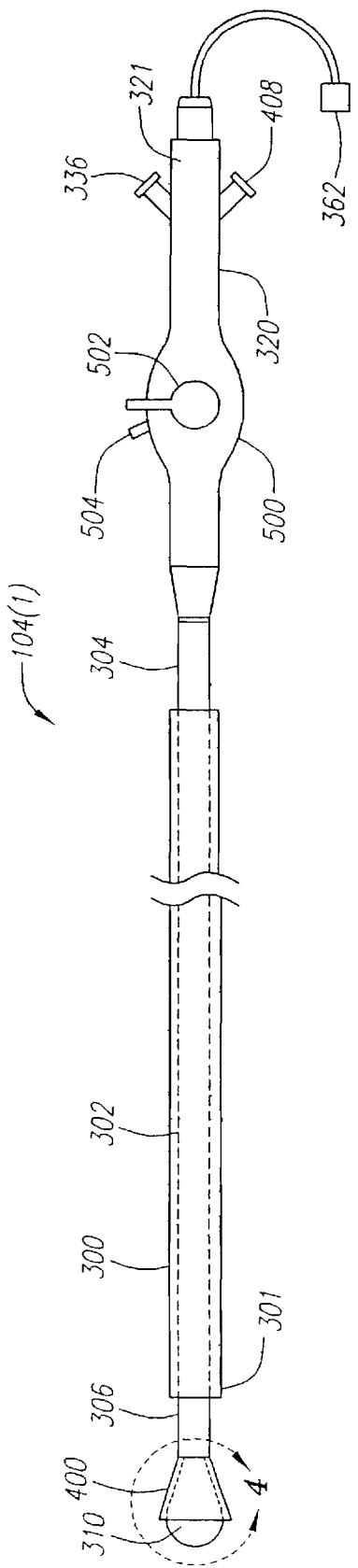
FIG. 3 is a plan view of an embodiment of an ablation catheter that may be used with the system of FIG. 1.

Turning now to FIG. 3, the details of the ablation catheter 104 will be described. The ablation catheter 104 includes an actuating sheath 300 having a lumen 301, and a catheter member 302 slidably disposed within the lumen 301 of the sheath 300. The ablation catheter 104 further includes an electrode structure 310 for transmitting ablation energy to adjacent tissue, and a vacuum actuated stabilizer 400 mounted to the distal end 306 of the catheter member 302 for stabilizing the electrode structure 310 relative to the tissue. The ablation catheter 104 further includes a handle assembly 320 mounted to the proximal end 304 of the catheter member 302. The handle assembly 320 includes a handle 321 for providing a means for the physician to manipulate the ablation catheter 104, and an electrical connector 362 coupled to the ablation source 108 for providing ablation energy to the electrode structure 310. The handle assembly 320 further includes a vacuum port 408 coupled to the vacuum 598 for generating a vacuum force for the stabilizer 400, and an inflation port 336 coupled to the pump 409 for supplying the electrode structure 310 with pressurized inflation medium.

The sheath 300 and the catheter member 302 are preferably made from a thermoplastic material, such as a polyurethane, a polyolefin or polyetherpolyamide block copolymer. In an alternative embodiment, the catheter member 302 is composed of an extrusion of wire braided plastic material and a flexible spring that is disposed within the extruded material.

The handle assembly 320 includes a steering mechanism 500 for steering the electrode structure 310. The steering mechanism 500 includes a steering lever 502 operable for steering of the electrode structure 310. The steering mechanism 500 further includes a locking lever 504 operable in a first position to lock the steering lever 502 in place, and in a second position to release the steering lever 502 from a locked configuration. Further details regarding this and other types of handle assemblies can be found in U.S. Pat. Nos. 5,254,088, and 6,485,455 B1, the entire disclosures of which are hereby expressly incorporated by reference.

The electrode structure 310 can be variously constructed. For example, FIGS. 4 and 5 illustrated one embodiment of an electrode structure 310(1). The electrode structure 310(1) includes an expandable-collapsible electrode body 330, which can be altered between an enlarged or expanded geometry (FIG. 4) when placed outside the lumen of the sheath 300, and a collapsed geometry (FIG. 5) when disposed within the lumen 301 of the sheath 300. In the illustrated embodiment, liquid pressure is used to inflate and maintain the expandable-collapsible body 330 in the expanded geometry. The electrode structure 310(1) further includes an actuating internal electrode 350 that supplies the body 330 with RF energy. Specifically, the internal electrode 350 supplies RF energy through the medium that is used to inflate the body 330, which is then conveyed through pores 370 in the body 330 to the surrounding tissue, as will be described in further detail below.

The internal electrode 350 is carried at a distal end 352 of a support member 354, which is fixedly secured within the lumen 332 of the catheter member 302 by cross bars 355 or similar structures. In an alternative embodiment, the electrode 350 can be carried by a structure (not shown) fixedly secured to the distal end 306 of the catheter member 302. In a further alternative embodiment, the electrode structure 310(1) does not include the cross bars 355, and the support member 354 is slidable within the lumen 332. This has the benefit of allowing the support member 354 to be removed from the interior 334 of the body 330, thereby allowing the body 330 to collapse into a lower profile. The interior electrode 350 is composed of a material that has both a relatively high electrical conductivity and a relatively high thermal conductivity. Materials possessing these characteristics include gold, platinum, platinum/iridium, among others. Noble metals are preferred. A RF wire 360 extends through the lumen 332 of the catheter member 302, and electrically couples the internal electrode 350 to the electrical connector 362 on the handle assembly 320 (see FIG. 3). The support member 354 and/or the electrode structure 310 may carry temperature sensor(s) (not shown) for sensing a temperature of a liquid inflation medium 338 during use.

The distal end of the catheter lumen 332 is in fluid communication with the hollow interior 334 of the expandable-collapsible body 330, and the proximal end of the lumen 332 is in fluid communication with the port 336 on the handle assembly 320 (see FIG. 3). During use, the inflation medium 338 is conveyed under positive pressure by the pump 409 through the port 336 and into the lumen 332. The liquid medium 338 fills the interior 334 of the expandable-collapsible body 330, thereby exerting interior pressure that urges the expandable-collapsible body 330 from its collapsed geometry to its enlarged geometry.

The liquid medium 338 used to fill the interior 334 of the body 330 establishes an electrically conductive path, which conveys radio frequency energy from the electrode 350. In conjunction, the body 330 comprises an electrically non-conductive thermoplastic or elastomeric material that contains the pores 370 on at least a portion of its surface. The pores 370 of the body 330 (shown diagrammatically in enlarged form in FIGS. 4 and 5 for the purpose of illustration) establish ionic transport of ablation energy from the internal electrode 350, through the electrically conductive medium 338, to tissue outside the body 330.

Preferably, the medium 338 possesses a low resistivity to decrease ohmic loses, and thus ohmic heating effects, within the body 330. In the illustrated embodiment, the medium 338 also serves the additional function as the inflation medium for the body 330, at least in part. The composition of the electrically conductive medium 338 can vary. In one embodiment, the medium 338 comprises a hypertonic saline solution, having a sodium chloride concentration at or near saturation, which is about 9%-15% weight by volume. Hypertonic saline solution has a low resistivity of only about 5 ohm-cm, compared to blood resistivity of about 150 ohm-cm and myocardial tissue resistivity of about 500 ohm-cm. Alternatively, the composition of the electrically conductive liquid medium 338 can comprise a hypertonic potassium chloride solution. This medium, while promoting the desired ionic transfer, requires closer monitoring of rate at which ionic transport occurs through the pores, to prevent potassium overload. When hypertonic potassium chloride solution is used, it is preferred to keep the ionic transport rate below about 10 mEq/min.

The size of the pores 370 can vary. Pore diameters smaller than about 0.1 um, typically used for blood oxygenation, dialysis, or ultrafiltration, can be used for ionic transfer. These small pores, which can be visualized by high-energy electron microscopes, retain macromolecules, but allow ionic transfer through the pores in response to an applied RF field. With smaller pore diameters, pressure driven liquid perfusion through the pores 370 is less likely to accompany the ionic transport, unless relatively high pressure conditions develop with the body 330.

Larger pore diameters, typically used for blood microfiltration, can also be used for ionic transfer. These larger pores, which can be seen by light microscopy, retain blood cells, but permit passage of ions in response to the applied RF field. Generally, pore sizes below 8 um will block most blood cells from crossing the membrane. With larger pore diameters, pressure driven liquid perfusion, and the attendant transport of macromolecules through the pores 370, is also more likely to occur at normal inflation pressures for the body 330. Still larger pore sizes can be used, capable of accommodating formed blood cell elements. However, considerations of overall porosity, perfusion rates, and lodgment of blood cells within the pores of the body 330 must be taken more into account as pore size increases.

Conventional porous, biocompatible membrane materials used for blood oxygenation, dialysis, and blood filtration, such as plasmapheresis, can serve as the porous body 330. The porous body 330 can also be made from, for example, regenerated cellulose, nylon, polycarbonate, polytetrafluoroethylene (PTFE), polyethersulfone, modified acrylic copolymers, and cellulose acetate. Alternatively, porous or microporous materials may be fabricated by weaving a material (such as nylon, polyester, polyethylene, polypropylene, fluorocarbon, fine diameter stainless steel, or other fiber) into a mesh having the desired pore size and porosity. The use of woven materials is advantageous, because woven materials are very flexible.

Figure 6:
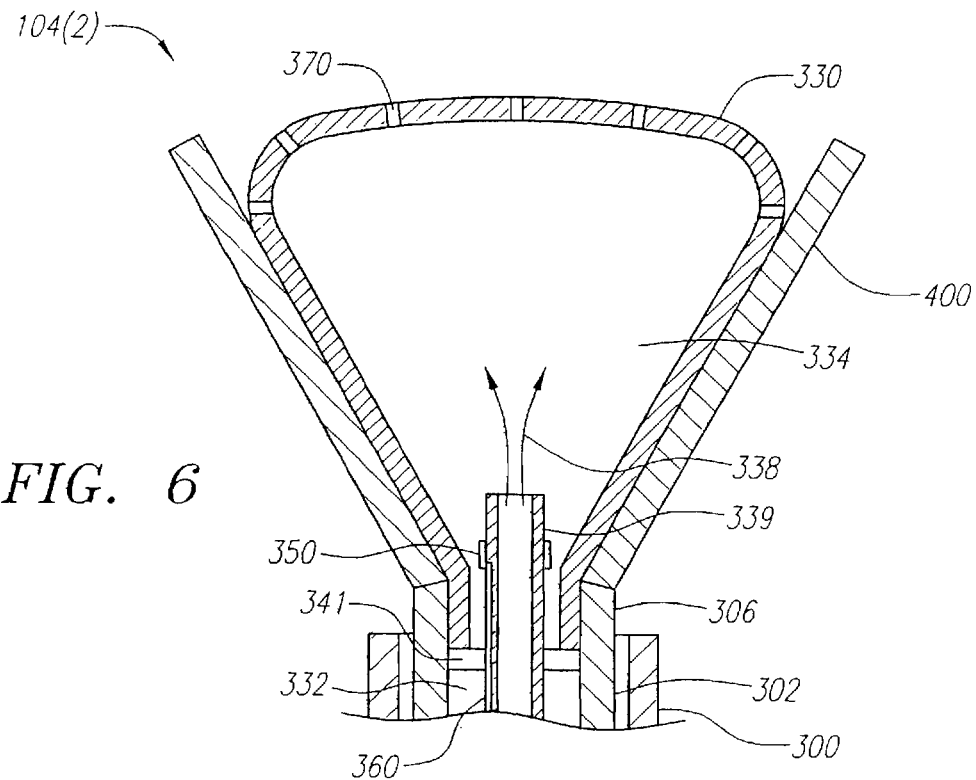
FIG. 6 is a cross-sectional view of an alternative embodiment of an ablation catheter that may be used with the system of FIG. 1.

Referring now to FIG. 6, another embodiment of a catheter 104(2) will be described. Instead of using the lumen 332 of the catheter member 302 for delivery of the liquid medium 338, as described in the previous embodiment, the ablation catheter 104(2) includes a separate delivery tube 339 positioned coaxially within the lumen 332 of the catheter member 302 for delivering the liquid medium 338. In this case, the internal electrode 350 is carried at a distal end of the tube 339. The electrode structure 310 also includes a sealer 341 secured to an interior surface of the catheter member 302. In the illustrated embodiment, the tube 339 is secured to the sealer 341, which has a shape and size configured to prevent delivered medium 338 from escaping from the interior 334 of the body 330.

The tube 339 is slidably secured to the sealer 341. This has the benefit of allowing the delivery tube 339 to be removed from the interior 334 of the body 330, thereby allowing the body 330 to collapse into a lower profile. In this case, the sealer 341 has a shape and size configured to prevent delivered medium 338 from escaping from the interior 334 of the body 330, while allowing the tube 339 to slide therethrough. Alternatively, if a sliding arrangement between the tube 339 and the body 330 is not required or desired, the delivery tube 339 can be secured to the proximal end of the body 330.

Figure 7:
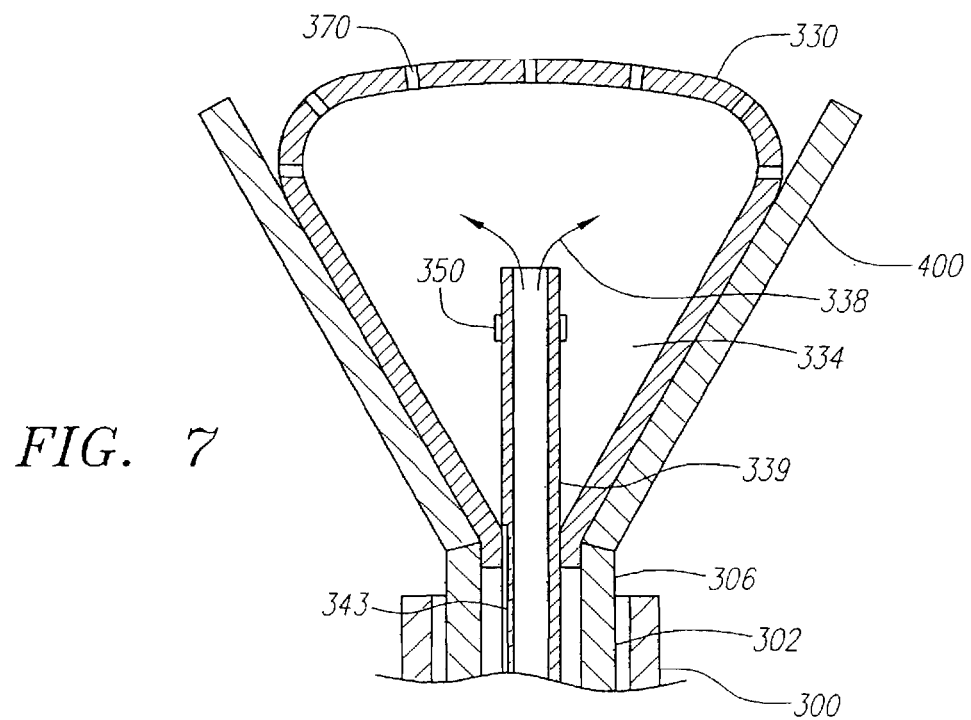
FIG. 7 is a cross-sectional view of a variation of the ablation catheter of FIG. 6.

The proximal end of the delivery tube 339 is coupled to the pump 409 during use. The body 330 can be inflated by the medium 338 delivered via the delivery tube 339, and deflated by discharging the medium 338 also through the delivery tube 339. In an alternative embodiment, the catheter 104(2) does not include the sealer 341, and the lumen 332 of the catheter member 302 outside the delivery tube 339 can be used to return medium to the proximal end of the ablation catheter 104(1). Alternatively, the delivery tube 339 may have an outer diameter that is substantially the same as the opening at the proximal end of the body 330, thereby forming a substantially water-tight interface between the delivery tube 339 and the body 330 (FIG. 7). In this case, the tube 339 includes a separate discharge lumen 343 disposed within the wall of the tube 339 for carrying medium 338 away from the body 330.

Figure 8:
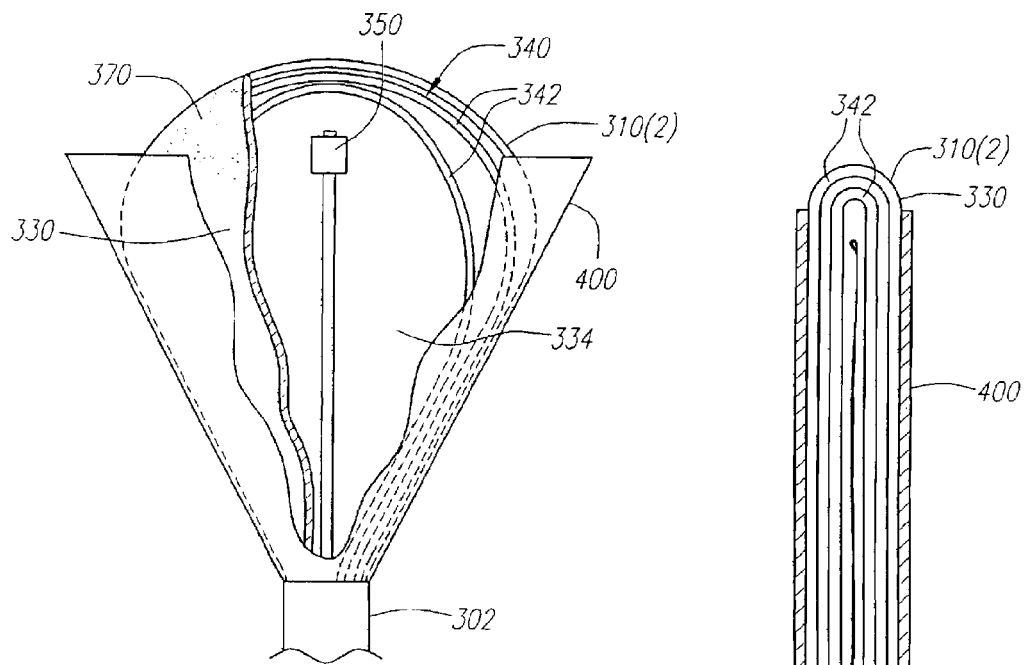
FIG. 8 is a partial cut-away view of an alternative embodiment of an electrode structure that can be used in the ablation catheter of FIG. 3.
Figure 9:
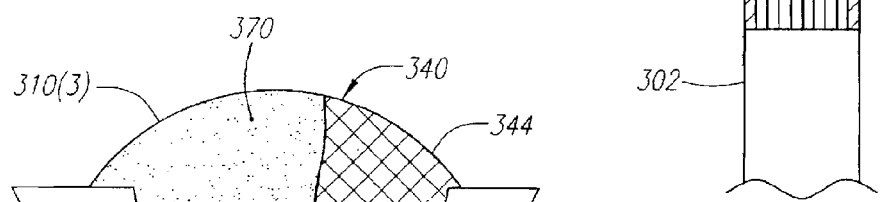
FIG. 9 is a cross-sectional view of the electrode structure of FIG. 8.
Figure 10:
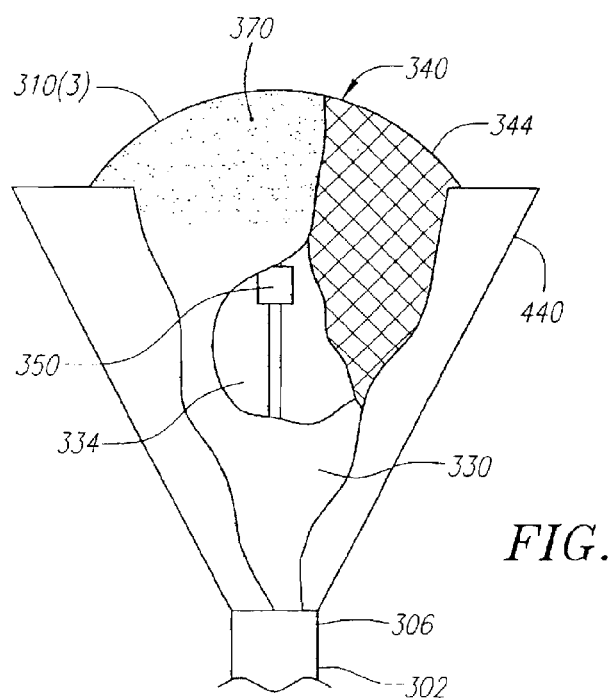
FIG. 10 is a partial cut-away view of still another alternative embodiment of the electrode structure of FIG. 3.

As FIGS. 8-10 show, the electrode structure 310 can include, if desired, a normally open, yet collapsible, interior support structure 340 to apply internal force to augment or replace the force of liquid medium pressure to maintain the body 330 in the expanded geometry. The form of the interior support structure 340 can vary. It can, for example, comprise an assemblage of flexible spline elements 342, as shown in the electrode structure 310(2) of FIG. 8 (expanded geometry) and FIG. 9 (collapsed geometry), or an interior porous, interwoven mesh or an open porous foam structure 344, as shown in the electrode structure 310(3) of FIG. 10. The interior support structure 340 is located within the interior 334 of the body 330 and exerts an expansion force to the body 330 during use. Alternatively, the interior support structure 340 can be embedded within the wall of the body 330. The interior support structure 340 can be made from a resilient, inert material, like nickel titanium (commercially available as Nitinol material), or from a resilient injection molded inert plastic or stainless steel. The interior support structure 340 is preformed in a desired contour and assembled to form a three dimensional support skeleton.

Figure 11A:
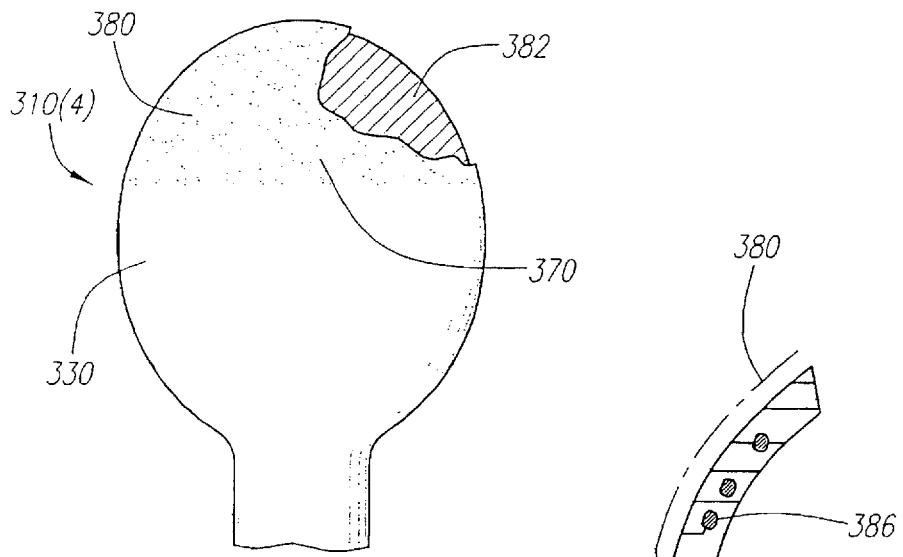
FIG. 11A is a partial cut-away view of yet another alternative embodiment of an electrode structure that can be used in the ablation catheter of FIG. 3.
Figure 11C:
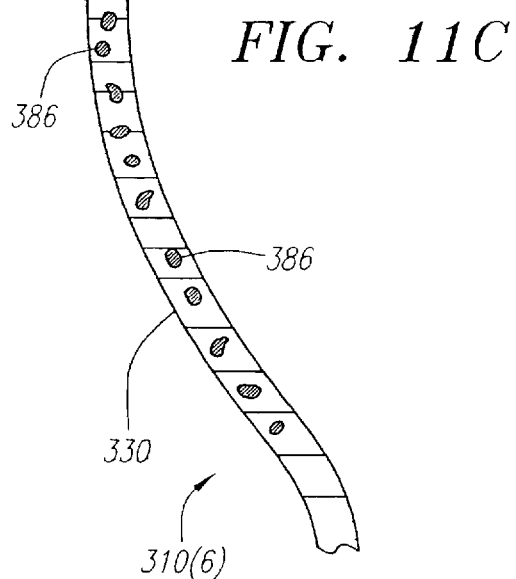
FIG. 11C is a partial cut-away view of yet another alternative embodiment of an electrode structure that can be used in the ablation catheter of FIG. 3.
Figure 11B:
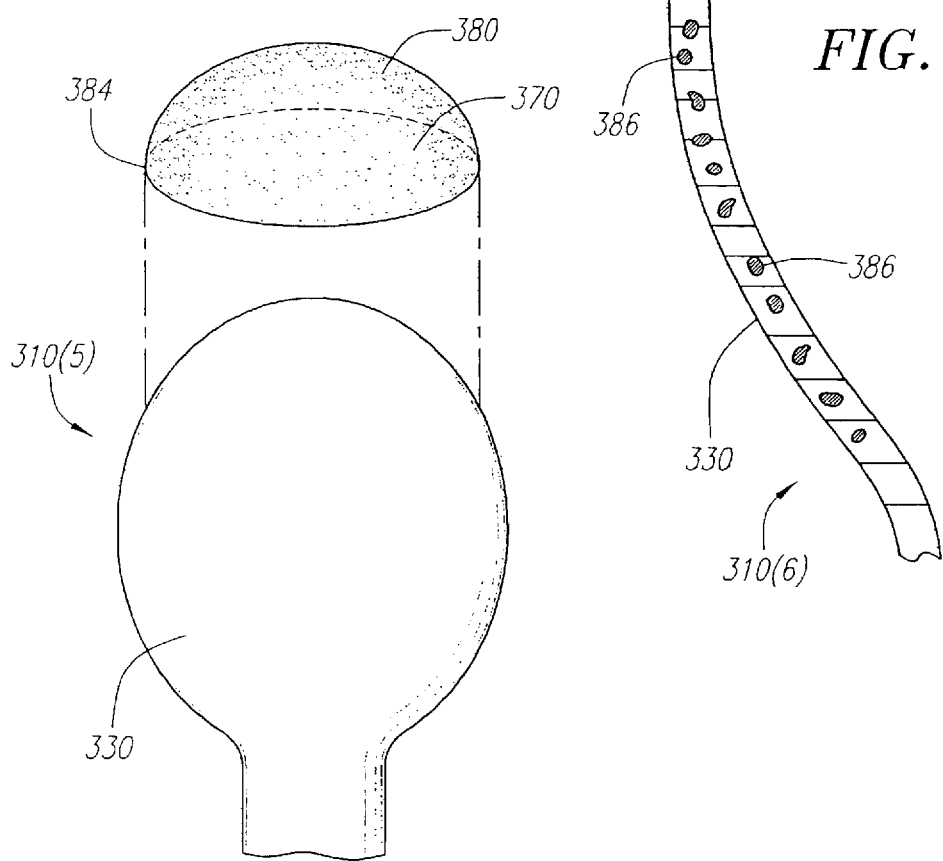
FIG. 11B is a partial cut-away view of yet another alternative embodiment of an electrode structure that can be used in the ablation catheter of FIG. 3.
Figure 12:
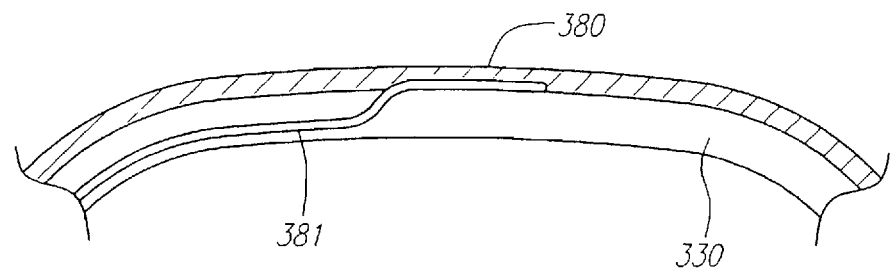
FIG. 12 is a partial side cross-sectional view of the electrode structure of FIG. 11A, showing the RF wire embedded with the wall of the body.
Figure 13:
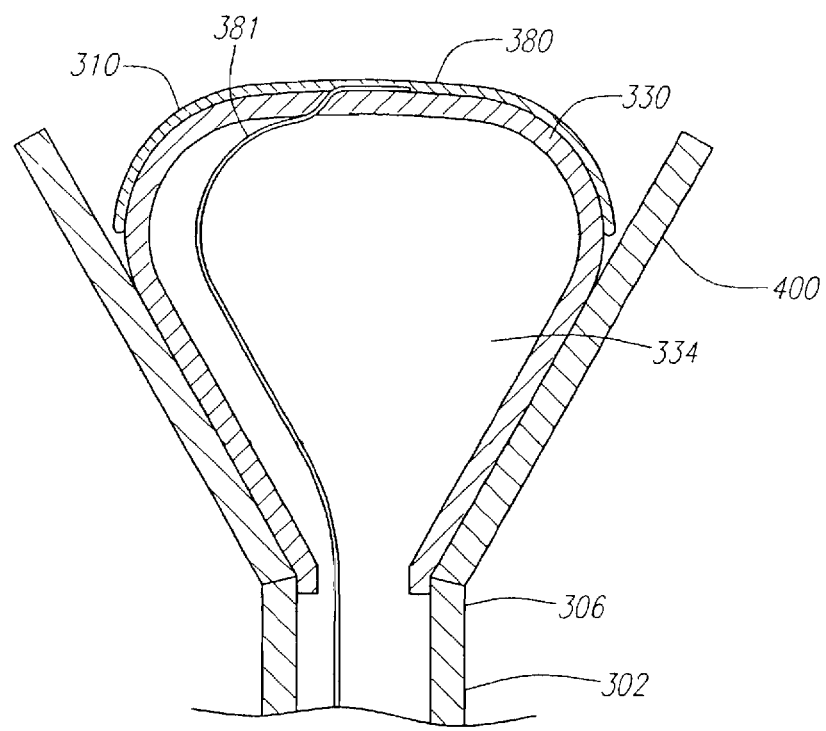
FIG. 13 is a partial side cross-sectional view of the electrode structure of FIG. 11A, showing the RF wire carried within the interior of the body.

Referring now to FIGS. 11-13, further embodiments of an electrode structure 310 are described. The stabilizer 400 is not shown for the purpose of clarity. Rather than having a porous body 330 and an interior electrode 350, as with the previous embodiments, the electrode structures 310 illustrated in FIGS. 11A-11C comprise a non-porous expandable-collapsible body 330, and an electrically conductive layer associated with the non-porous body 330.

For example, FIG. 11A illustrates one embodiment of an electrode structure 310(4) that includes an electrically conducting shell 380 disposed upon the exterior of the formed body 330. The electrode structure 310 also includes a RF wire 381 (FIGS. 12 and 13) that electrically connects the shell 380 to the ablation source 108. The RF wire 381 may be embedded within the wall (FIG. 12) of the body 330, or alternatively, be carried within the interior 334 of the body 330 (FIG. 13). Ablation energy is delivered from the ablation source 108, via the RF wire 381, to the shell 380.

In the illustrated embodiment, the shell 380 is deposited upon the surface of the body 330. Preferably, the shell 380 is not deposited on the proximal one-third surface of the body 330. This requires that the proximal surface of the body 330 be masked, so that no electrically conductive material is deposited there. This masking is desirable because the proximal region of the electrode structure 310 is not normally in contact with tissue. The shell 380 may be made from a variety of materials having high electrical conductivity, such as gold, platinum, and platinum/iridium. These materials are preferably deposited upon the unmasked, distal region of the body 330. Deposition processes that may be used include sputtering, vapor deposition, ion beam deposition, electroplating over a deposited seed layer, or a combination of these processes. To enhance adherence between the expandable-collapsible body 330 and the shell 380, an undercoating 382 is first deposited on the unmasked distal region before depositing the shell 380. Materials well suited for the undercoating 382 include titanium, iridium, and nickel, or combinations or alloys thereof.

FIG. 11B illustrates another embodiment of an electrode structure 310(5) in which the shell 380 comprises a thin sheet or foil 384 of electrically conductive metal affixed to the wall of the body 330. Materials suitable for the foil include platinum, platinum/iridium, stainless steel, gold, or combinations or alloys of these materials. The foil 384 preferably has a thickness of less than about 0.005 cm. The foil 384 is affixed to the body 330 using an electrically insulating epoxy, adhesive, or the like.

FIG. 11C illustrates still another embodiment of an electrode structure 310(6) in which all or a portion of the expandable-collapsible wall forming the body 330 is extruded with an electrically conductive material 386. Materials 386 suitable for coextrusion with the expandable-collapsible body 330 include carbon black and chopped carbon fiber. In this arrangement, the coextruded expandable collapsible body 330 is itself electrically conductive. An additional shell 380 of electrically conductive material can be electrically coupled to the coextruded body 330, to obtain the desired electrical and thermal conductive characteristics. The extra external shell 380 can be eliminated, if the coextruded body 330 itself possesses the desired electrical and thermal conductive characteristics. The amount of electrically conductive material coextruded into a given body 330 affects the electrical conductivity, and thus the electrical resistivity of the body 330, which varies inversely with conductivity. Addition of more electrically conductive material increases electrical conductivity of the body 330, thereby reducing electrical resistivity of the body 330, and vice versa.

The above described porous and non-porous expandable-collapsible bodies and other expandable structures that may be used to form the electrode structure 310 are described in U.S. Pat. Nos. 5,846,239, 6,454,766 B1, and 5,925,038, the entire disclosures of which are expressly incorporated by reference herein.

Figure 14:
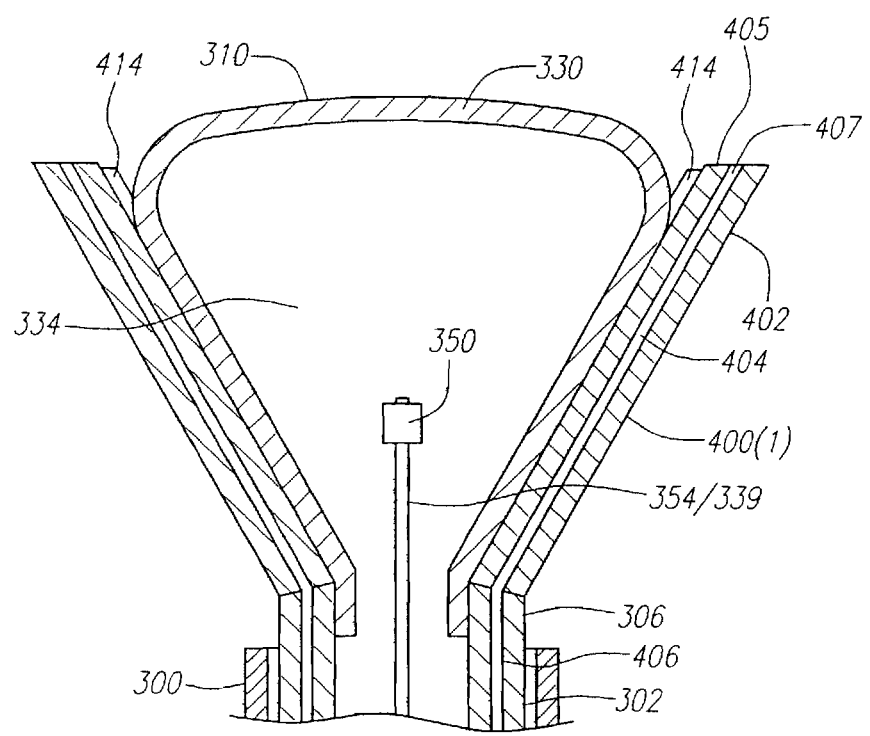
FIG. 14 is a cross-sectional view of an embodiment of the electrode structure and stabilizer of FIG. 3, showing the details of the stabilizer.
Figure 15:
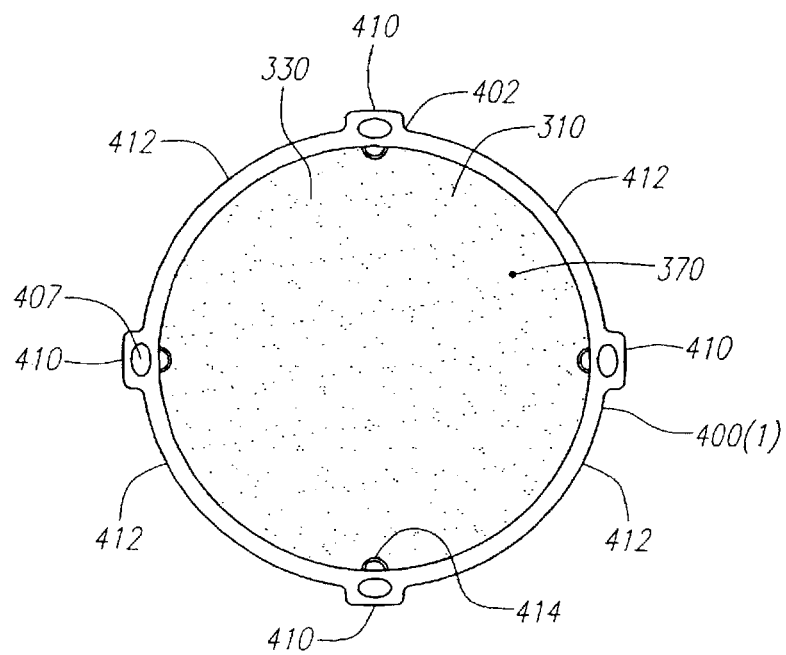
FIG. 15 is a top view of the electrode structure of FIG. 14.

Refer to FIGS. 14-18, the stabilizer 400 and the portion of the ablation catheter 104 in association with the stabilizer 400 will now be described. As shown in FIGS. 14 and 15, one embodiment of a stabilizer 400(1) includes a shroud 402 that is secured to the distal end 306 of the catheter member 302. The shroud 402 circumscribes at least a portion of the expandable-collapsible body 330, thereby substantially preventing ablation energy from dissipating to surrounding tissues beyond the target tissue to be ablated. The stabilizer 400(1) further comprises a plurality of vacuum ports 407 (here, four) associated with a distal edge 405 of the shroud 402, and a plurality of respective vacuum lumens 404 longitudinally extending within a wall of the shroud 402 in fluid communication with the vacuum ports 407. The stabilizer 400(1) includes an optional temperature sensing element 414, such as a thermocouple or thermistor, secured to the shroud 402. The temperature sensing elements 414 may be used to monitor a tissue temperature.

To provide vacuum force to the stabilizer 400(1), the ablation catheter 104 comprises a main vacuum lumen 406 embedded with the wall of the catheter member 302. The lumen 406 is in fluid communication between the vacuum lumens 404 on the shroud 402 and the vacuum port 408 located on the handle assembly 320. During use of the ablation catheter 104, the vacuum port 408 is coupled to the vacuum 598, which generates a vacuum or a vacuum force within the vacuum lumens 404 of the stabilizer 400(1).

The shroud 402 is made from a material having low electrical conductivity, such as a polymer, plastic, silicone, or polyurethane. The shroud 402 has enlarged planar regions 410 for carrying the vacuum lumens 404, and thinner planar regions 412 for allowing the shroud 402 to fold into a low profile during use (FIG. 15). Alternatively, if the vacuum lumens 404 are sufficiently small, the shroud 402 can have a substantially uniform wall thickness. Although four enlarged planar regions 410 are shown, the shroud 402 can have fewer or more than four planar regions 410, depending on the number of vacuum lumens 404.

In the illustrated embodiment, the stabilizer 400(1) is secured to the exterior surface of the expandable-collapsible body 330. In this configuration, the stabilizer 400 will be pushed open by the body 330 to its expanded configuration when the body 330 is inflated, and pulled to its collapsed configuration when the body 330 is deflated. Alternatively, the stabilizer 400(1) is not secured to the body 330, in which case, the stabilizer 400(1) will be pushed open by a bearing force exerted by the body 330 when the body 330 is expanded, and will assume a collapsed configuration when the electrode structure 310 is confined within a lumen of the sheath 300.

Figure 16:
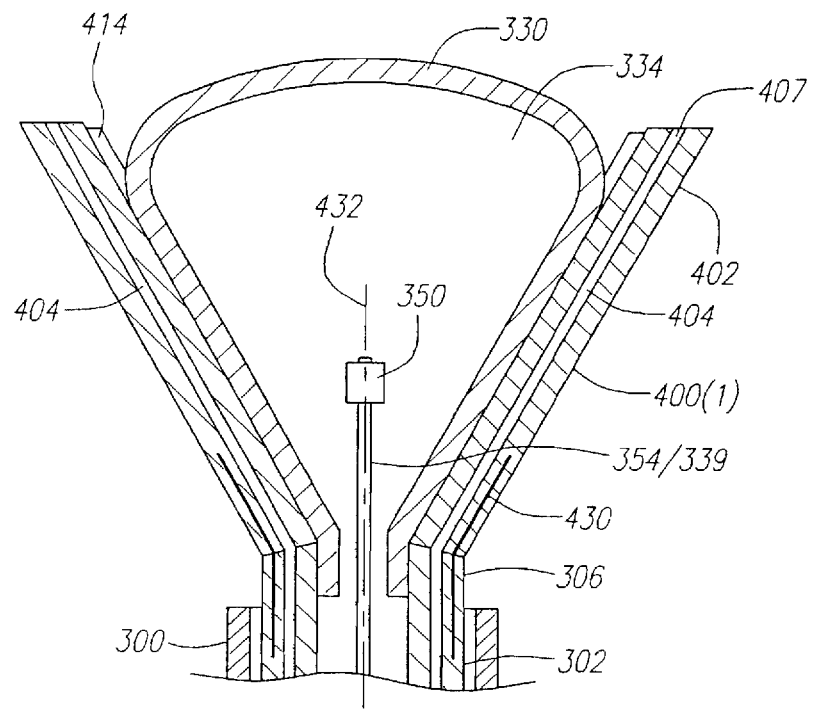
FIG. 16 is a cross-sectional view of a variation of the stabilizer of FIG. 14.

As shown in FIG. 16, the stabilizer 400(1) optionally includes support wires 430, which are partially embedded within the wall of the shroud 402 and partially within the wall of the catheter member 302. The support wires 430 can be made from a resilient material, such as metal or plastic. Nitinol is particularly preferred. In one embodiment, the support wires 430 are preformed to have a shape that is substantially rectilinear. In this case, the shroud 402 will remain substantially in its collapsed configuration until pushed to open into an expanded configuration by the expandable-collapsible body 330 when the body 330 is expanded. Such configuration has the benefit of allowing the electrode structure 310 to assume its collapsed configuration more easily. If the support wires 430 are made stiff enough, the electrode structure 310 together with the stabilizer 400(1) can assume their collapsed configurations without the use of the sheath 300. In this case, the sheath 300 is optional and the ablation catheter 104 does not include the sheath 300. In an alternative embodiment, the support wires 430 are preformed to have a bent shape that flares away from a centerline 432 at the distal end 306 of the catheter member 302. In this case, the stabilizer 400(1) will assume a collapsed configuration when resided within a lumen of a sheath 300, and will have a tendency to open into the expanded configuration when it extends distally from the sheath 300. Such configuration has the benefit of allowing the electrode structure 310 to assume its expanded configuration more easily.

Figure 17:
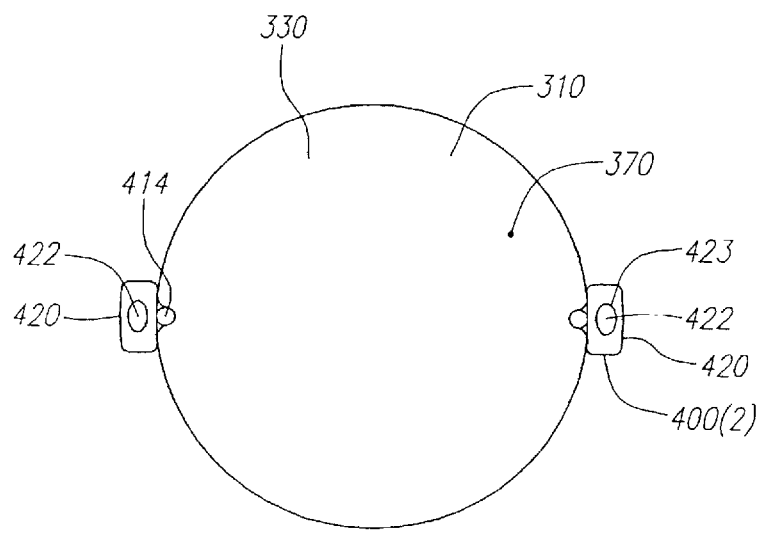
FIG. 17 is a top view of an alternative embodiment of the stabilizer of FIG. 3.

FIG. 17 shows another embodiment of a stabilizer 400(2) that does not continuously circumscribe a portion of the body 330 as did the previously described stabilizer 400(1). Instead, the stabilizer 400(2) comprises a plurality of tubes 420 (in this case, two) that extend along the length of the body 330. The tubes 430 may or may not be secured to the body 330. Each of the tubes 430 has a vacuum lumen 422 and an associated vacuum port 423 at its distal end. The proximal end of each tube 420 is in fluid communication with the vacuum port 408 located on the handle assembly 320 (shown in FIG. 3). The tubes 420 include optional support wires 430 to provide a pre-shaped geometry, as previously described with respect to the shroud 402 of the stabilizer 400(1).

Figure 18:
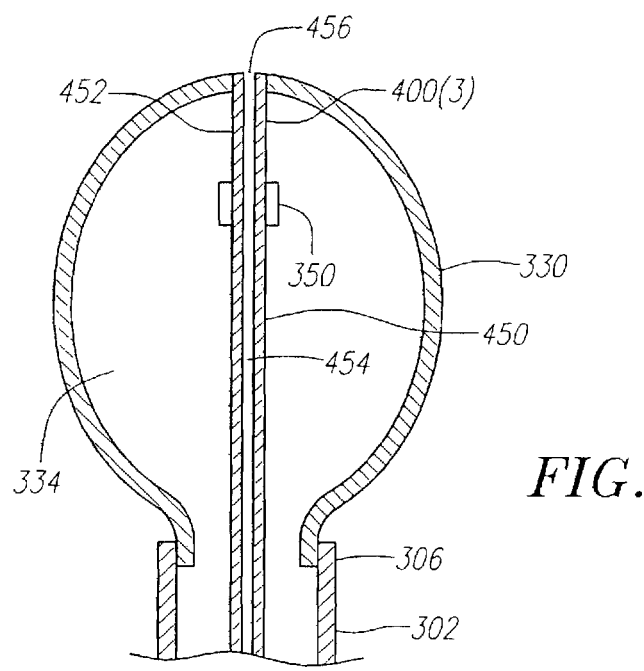
FIG. 18 is a cross-sectional view of another embodiment of the electrode structure of FIG. 3, showing the stabilizer internal to the body.

In all of the above-described embodiments, the stabilizer 400 is exterior to the expandable-collapsible body 330. FIG. 18 shows another embodiment of a stabilizer 400(3) that is internal to the body 330. As shown in the illustrated embodiment, the stabilizer 400(3) includes a vacuum tube 450 located within the interior 334 of the expandable-collapsible body 330. The vacuum tube 450 includes a distal end 452 that is secured to the distal portion of the body 330. The tube 450 has a vacuum lumen 454 and an associated vacuum port 456 at its distal end. The proximal end of the tube 420 is in fluid communication with the vacuum port 408 at the handle assembly 320 (shown in FIG. 3). The vacuum tube 450 carries the electrode 350, thus obviating the need for the previously described support member 354.

Although the ablation catheter 104 has been described as having electrode structures 310 with expandable-collapsible bodies, it should be noted that the ablation catheter 104 can have other electrode structure configurations. For example, FIG. 19A illustrates another embodiment of an ablation catheter 104(3), which includes a catheter member 462, an electrode structure 310(7) and stabilizer 400(4) mounted to the distal end 464 of the catheter member 462, and a handle assembly 461 mounted to the proximal end 465 of the catheter member 462. The handle assembly 461 is similar to the previously described handle assembly 320, with the exception that it does not include a fluid port, since there is no expandable/collapsible body.

The electrode structure 310(7) does not include an expandable-collapsible body, but rather a rigid cap-shaped electrode 460 mounted to the distal tip of the catheter member 462. The electrode structure 310(7) further comprises a RF wire 468 that is electrically coupled between the electrode 460 and the electrical connector 362 on the handle assembly 461. The RF wire 468 extends through a lumen 466 of the catheter member 462. The stabilizer 400(4) includes one or more vacuum lumens 470 (in this case, two) embedded within the wall of the catheter member 462. The distal ends of the vacuum lumens 470 terminate in vacuum ports 472, and the proximal ends of the vacuum lumens 470 are in fluid communication with the vacuum port 408 on the handle assembly 461.

In an alternative embodiment, the lumen 466 may also be used to deliver cooling medium to the electrode 460 for active cooling the electrode 460 during use. In the illustrated embodiment, the electrode 460 does not have any outlet port, and therefore, the ablation catheter 104(3) can be used to perform closed loop cooling in which cooling medium is delivered to the electrode 460 and circulate back to a proximal end of the ablation catheter 104(3). Alternatively, the electrode 460 can have one or more outlet ports for performing open loop cooling in which cooling medium is delivered to the electrode 460 and is at least partially discharged through the outlet port for cooling the outside of the electrode 460. Ablation catheters capable of performing closed loop cooling and open loop cooling are described in U.S. Pat. No. 5,800,432, the entire disclosure of which is expressly incorporated by reference herein.

Figure 19B:
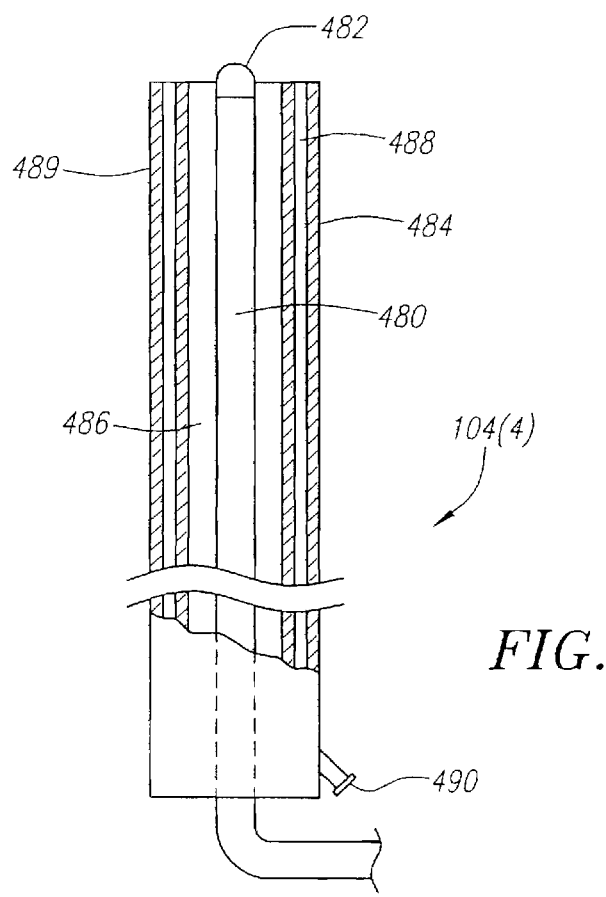
FIG. 19B is a cross-sectional view of another embodiment of an ablation catheter that may be used with the system of FIG. 1.
Figure 19A:
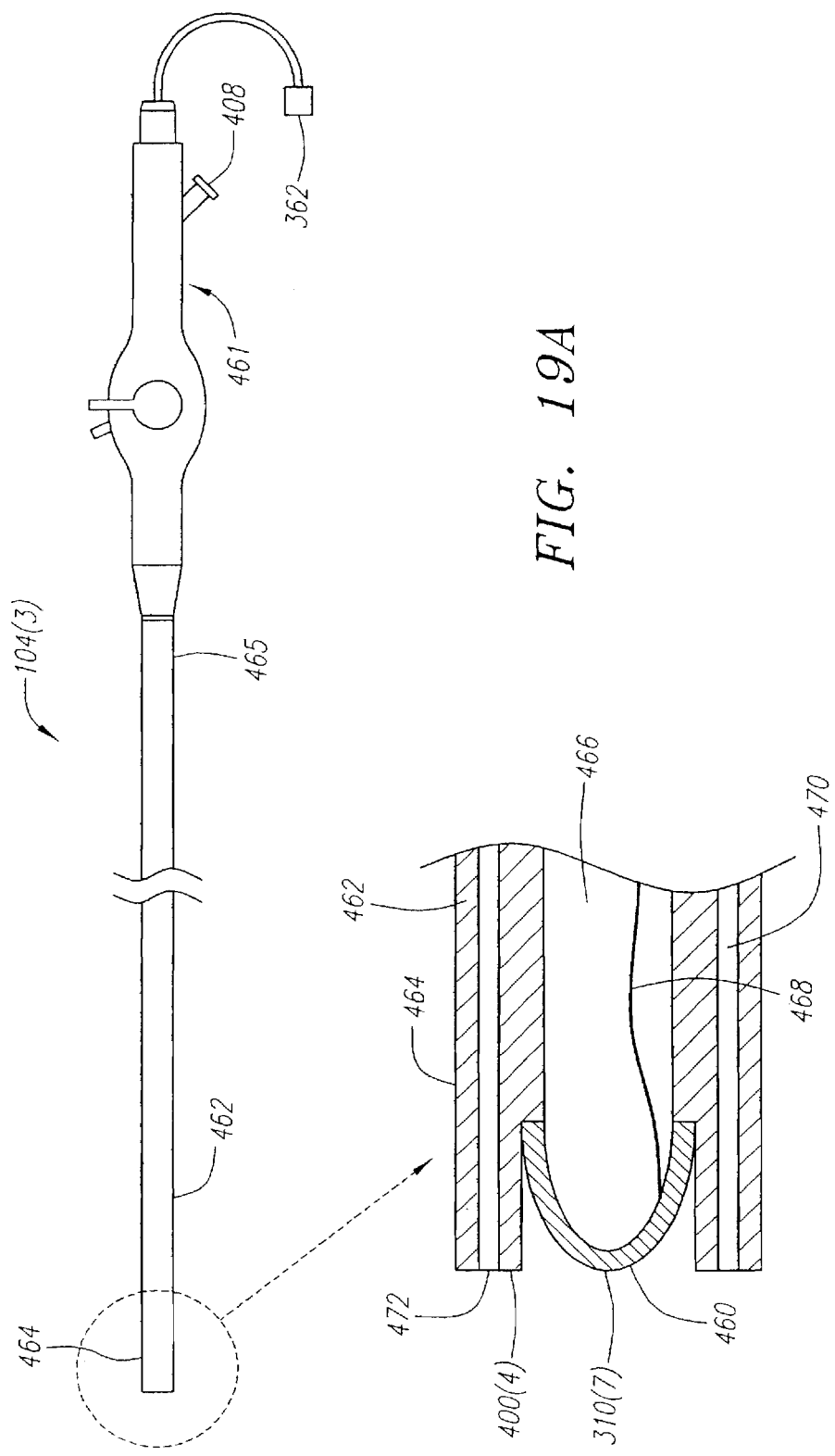
FIG. 19A shows another embodiment of an ablation catheter that may be used with the system of FIG. 1.
Figure 20:
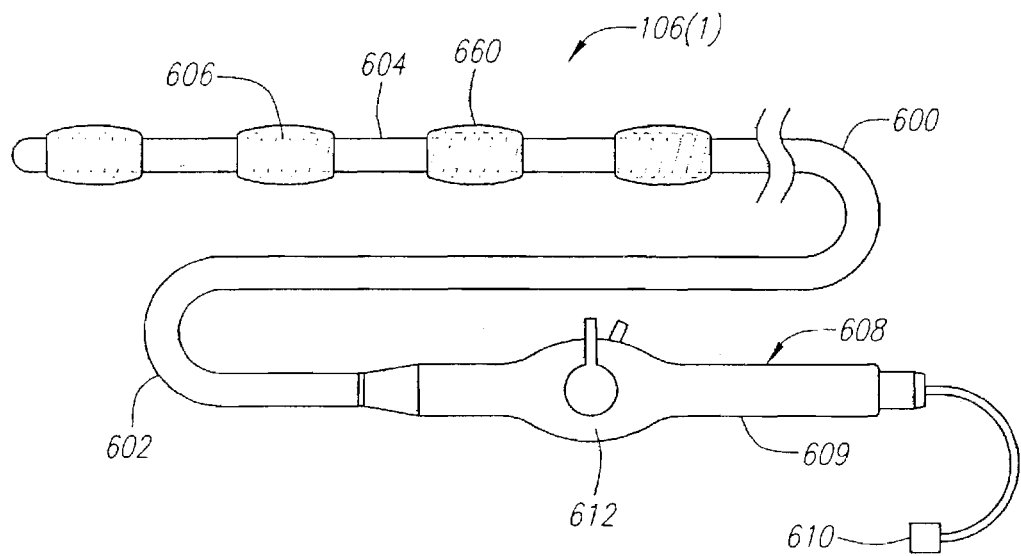
FIG. 20 is a top view of an embodiment of a ground probe that may be used with the system of FIG. 1.

FIG. 19B shows another embodiment of the ablation catheter 104(4), which is similar to the previously described ablation catheter 104(3), with the exception that it includes a sheath 484 and a catheter member 480 that is slidably disposed within the lumen 486 of the sheath 484. Rather than being disposed within the catheter member 480, the vacuum lumens 488 are disposed along the length of the sheath 484. In this case, the distal end 489 of the sheath 484 acts as the stabilizer. The sheath 484 also includes a vacuum port 490 that is in fluid communication with the vacuum lumens 488. It should be noted that the ablation device that can be used with the system 100 should not be limited to the embodiments of the ablation catheters 104(1)-104(4) discussed previously, and that other ablation devices known in the art may also be used. For examples, ablation catheters such as modified versions of those described in U.S. Pat. Nos. 5,800,432, 5,925,038, 5,846,239 and 6,454,766 B1, can be used with the system 100.

The Ground Probe

The ground catheter 106 will now be described with reference to FIGS. 20-26. In the embodiment shown in FIGS. 20 and 21, a ground catheter 106(1) includes a catheter member 600 having a proximal end 602 and a distal end 604, a plurality of electrode elements 606 carried on the distal end 604, and a handle assembly 608 secured to the proximal end 602. The catheter member 600 is made of, for example, a polymeric, electrically nonconductive material, such as polyethylene or polyurethane or PEBAX™ material (polyurethane and nylon). The handle assembly 608 includes a handle 609 for providing a means for the physician to manipulate the catheter member 600, and an electrical connector 610 coupled to the ablation source 108 for providing ablation energy to the electrode elements 606. The handle assembly 608 also includes a steering mechanism 612 for steering the distal end 604. The steering mechanism 612 is similar to the steering mechanism 500 discussed previously with reference to the ablation catheter 104. Furthermore, the ground catheter 106(1) may carry temperature sensor(s) (not shown) for monitoring a temperature of a tissue.

The electrode elements 606 function as indifferent electrodes and are configured to complete an electrical path from within a body of a patient. Each electrode element 606 has a suitable dimension along the length of the catheter member 600, e.g., 2 inches. The electrode elements 606 can be assembled in various ways. In the illustrated embodiment, the electrode elements 606 are arranged in a spaced apart, segmented relationship along the catheter member 600. Specifically, the electrode elements 606 comprise spaced apart lengths of closely wound, spiral coils wrapped about the catheter member 600 to form an array of generally flexible electrode elements 606. The coils are made of electrically conducting material, like copper alloy, platinum, or stainless steel, or compositions such as drawn-filled tubing. The electrically conducting material of the coils can be further coated with platinum-iridium or gold to improve its conductive properties and biocompatibility.

Alternatively, the segmented electrode elements 606 can each comprise solid rings of conductive material, like platinum, which makes an interference fit about the catheter member 600. Even more alternatively, the electrode segments 606 can comprise a conductive material, like platinum-iridium or gold, coated upon the catheter member 600 using conventional coating techniques or an ion beam assisted deposition (IBAD) process.

Figure 21:
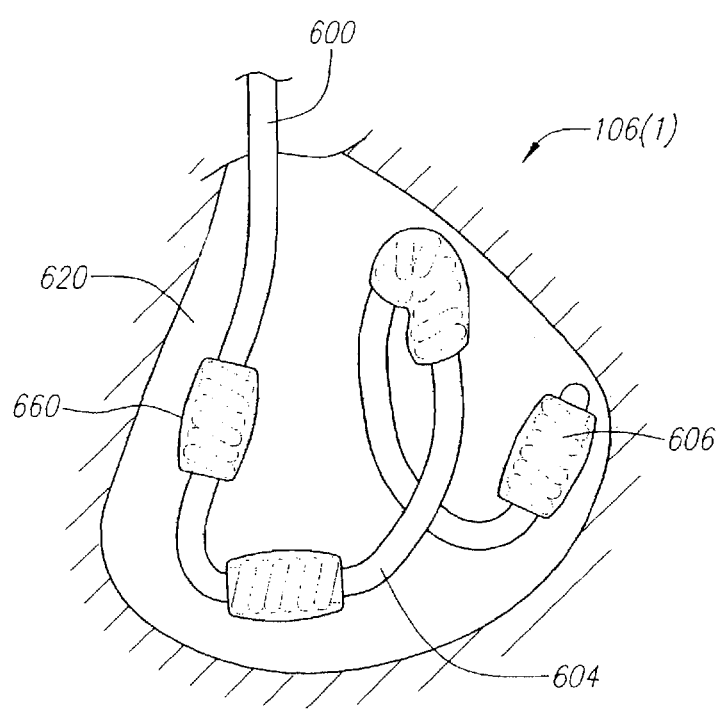
FIG. 21 is a partial side view of the ground probe of FIG. 20, showing the distal region of the sleeve folded within a body lumen.

Because the electrode elements 606 function as indifferent electrodes for returning energy to the ablation source 108, it would be desirable to maximize the space occupied by the electrode elements 606 and the number of electrode elements 606 within such space. Towards this end, the distal end 604 of the catheter member 600 and/or the electrode elements 606 is made sufficiently flexible such that the distal end 604 of the catheter member 600 can assume a configuration to at least partially fill a body cavity 620, as shown in FIG. 21.

Figure 22:
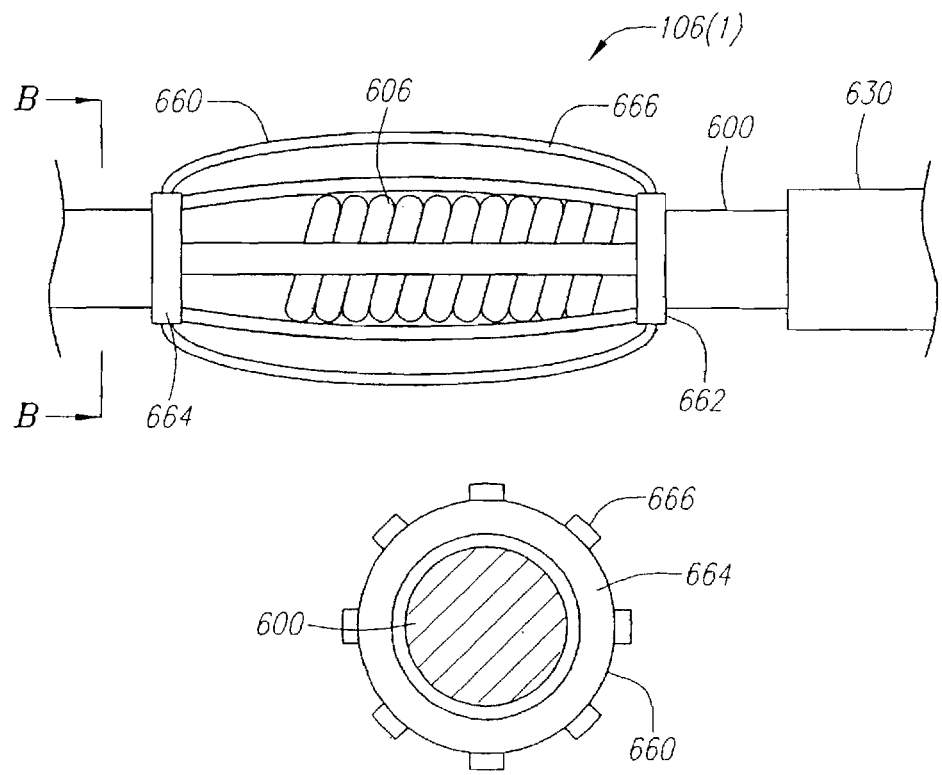
FIG. 22 is a partial side view of another embodiment of the ground probe of FIG. 20, showing the ground probe having a cage assembly.

To prevent the heated electrode elements 606 of the ground catheter 106(1) from damaging healthy tissue, the ground catheter 106(1) further includes a cage assembly 660 disposed around each electrode 606 to prevent it from making contact with tissue, and a sheath 630 for deploying the cage assembly 660. As shown in FIG. 22, the cage assembly 660 includes a proximal end 662, a distal end 664, and a plurality of struts 666 secured between the proximal end 662 and the distal end 664. At least one of the proximal end 662 and the distal end 664 is a ring element (FIG. 22). In the illustrated embodiment, the cage assembly 660 has eight struts. In alternative embodiments, the cage assembly 660 may have more or less than eight struts 666. The struts 666 are made from a non-electrically conductive and elastic material, such as a polymer. Alternatively, if insulation is provided between the cage assembly 660 and the electrode elements 606, the struts 666 can also be made from metal, such as stainless steel or Nitinol.

Figure 23:
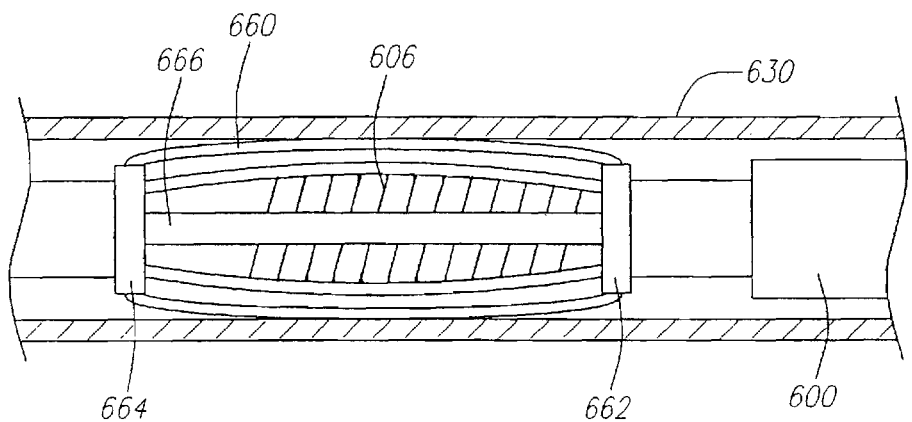
FIG. 23 is a partial side view of the ground probe of FIG. 22, showing the cage assembly having a collapsed configuration.

The cage assembly 660 assumes an expanded configuration when it is outside the sheath 630 (FIG. 22). The cage assembly 660, in its expanded configuration, prevents the electrode elements 606 from making contact with adjacent tissue during use. The spacing between the struts 666 allow medium, such as blood or other bodily fluid, to flow through and make contact with the electrode elements 606. Since blood and other bodily fluid contains ions, allowing blood or other bodily fluid to make contact with the electrode elements 606 assists completion of the current path between the electrode structure 310 and the electrode elements 606. The proximal end 662 and the distal end 664 are fixedly and slidably secured, respectively, to the catheter member 600. When the catheter member 600 is retracted proximally relative to the sheath 630, the sheath 630 compresses the struts 666 and causes the distal end 664 of the cage assembly 660 to slide distally relative to the catheter member 600 (FIG. 23). In an alternative embodiment, the distal end 664 of the cage assembly 660 is fixedly secured to the catheter member 600 and the proximal end 662 is slidable relative to the catheter member 600.

Although in the previously described embodiment, the cage assembly 660 is shown to at least partially cover a single electrode element 606, in alternative embodiments, the cage assembly 660 partially covers more than one electrode element 606. Furthermore, it should be noted that the cage assembly 660 is not limited to the configurations shown previously. For example, in alternative embodiments, the cage assembly 660 can comprise a braided or woven material secured to the struts 666. In another embodiment, the cage assembly 660 can comprise a braided or woven material that is elastic, in which case, the cage assembly 660 does not include the struts 666. Also, in another embodiment, instead of a cage assembly, the ground catheter can include other types of protective element, such as a wire or a plate, that at least partially covers an electrode.

FIGS. 24-26 show another embodiment of a ground catheter 106(2) that may be used with the system 100 of FIG. 1. As shown in FIG. 24, the ground catheter 106(2) includes a sheath 630 having a lumen 632, and a catheter member 634 slidable within the lumen 632 of the sheath 630. The catheter 106(2) comprises a plurality of electrodes 636 mounted on the distal end of the catheter member 634. The catheter member 634 and electrode elements 636 are similar to the previously described catheter member 600 and the electrode elements 606. Although not shown, the catheter 106(2) may also include one or more cage assemblies at least partially covering one or more of the electrodes 636, as discussed previously.

The catheter 106(2) further comprises a resilient spring member 642 that is suitably connected between the distal end 640 of the sheath 630 and the distal tip 638 of the catheter member 634. In the illustrated embodiment, the spring member 642 comprises a wire made of an elastic material, such as Nitinol, and is secured to an interior surface of the sheath 630. Alternatively, the spring member 642 can also be secured to an exterior surface of the sheath 630 (FIG. 26). Also, in alternative embodiments, the spring member 642 may be a coil or an extension of the catheter member 634, and may be made of other elastic materials, such as metals or plastics.

As shown in FIG. 25, distal movement of the proximal end 644 of the catheter member 634 relative to the sheath 630 deploys the catheter member 634 out of the distal end 640 of the sheath 630, and forms the catheter member 634 into a loop shape to thereby deploy the electrodes 636. In an alternative embodiment, a wire (not shown) preformed into a desired shape may be placed within the catheter member 634, such that when the catheter member 634 is deployed out of the distal end 640, the catheter member 634 will bend into a desired configuration.

The above-described devices and other similar devices having loop forming capability that may be used with the system 100 are described in U.S. Pat. No. 6,330,473, as mentioned herein. Furthermore, in alternative embodiments, the ground catheter 106 does not include a cage assembly. For example, internal indifferent electrode device, such as that described in U.S. patent application Ser. No. 09/801,416, can also be used as the ground catheter 106. U.S. patent application Ser. No. 09/801,416 is hereby expressly incorporated by reference in its entirety.

Mapping Catheter

Turning now to FIGS. 27-29, the details of the mapping catheter 700 will be described. The mapping catheter 700 is configured for sensing electrical signals at a heart to thereby determine a target location at the heart to be ablated.

Figure 27A:
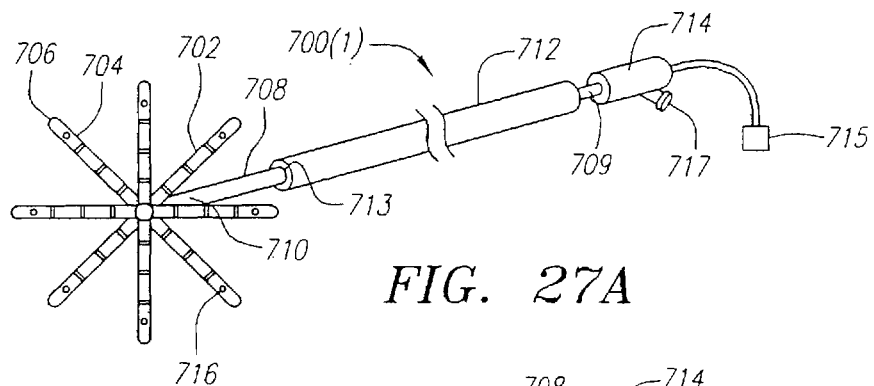
FIG. 27A is a perspective view of an embodiment of a mapping catheter that may be used with the system of FIG. 1.
Figure 27B:
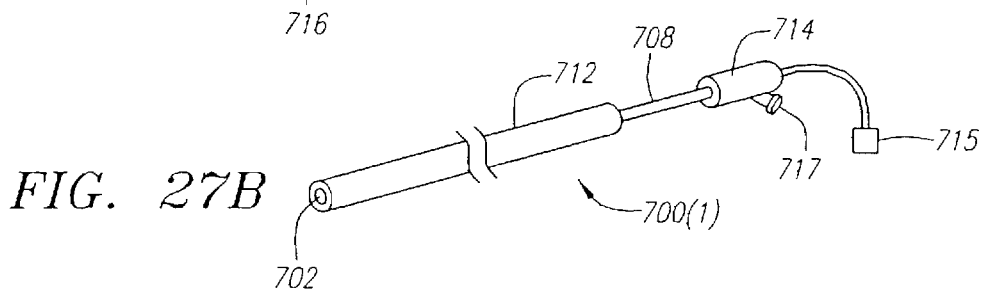
FIG. 27B is a perspective view of the mapping catheter of FIG. 27A.

FIG. 27A shows an embodiment of a mapping catheter 700(1) that may be used with the system 100 for sensing signals on a surface of a heart. The mapping catheter 700 includes an actuating sheath 712 having a lumen 713, and a catheter member 708 slidably disposed within the lumen 713 of the sheath 712. The catheter member 708 comprises a proximal end 709 and a distal end 710, and an electrode array structure 702 mounted to the distal end 710 of the catheter member 708. The electrode array structure 702 includes a plurality of resilient spline elements 704, with each spline element 704 carrying a plurality of mapping electrodes 706. Each of the spline elements 704 further includes a vacuum port 716 coupled to the vacuum 732 (shown in FIG. 1) via a lumen (not shown) carried within the spline element 704. The vacuum ports 716 are configured to apply a vacuum force to stabilize the array structure 702 relative to tissue as the mapping electrodes 706 sense electrical signals at the tissue. The number of spline elements 704 and electrodes 706 may vary, but in the illustrated embodiment, there are eight spline elements 704, with four mapping elements 706 on each spline element 704. The array 702 is configured to assume an expanded configuration, as shown in FIG. 27A, when it is outside the sheath 712. The size and geometry of the array 702 are configured such that the array 702 can at least partially cover the epicardial surface of a heart when it is in its expanded configuration. Because the mapping catheter 700(1) is not configured to be steered through vessels, as in the case with conventional mapping catheters, the array 702 can be made relatively larger to carry more mapping electrodes 706. The array 702 is also configured to be brought into a collapsed configuration by retracting the array 702 (i.e., proximally moving a handle 714 secured to the probe 708) into the lumen of the sheath 712 (FIG. 27B).

The mapping catheter 700(1) further includes a handle assembly 714 mounted to the proximal end 709 of the catheter member 708. The handle assembly 714 includes an electrical connector 715 coupled to the processor 730 for processing signals sensed by the mapping electrodes 706 to thereby determine a target site to be ablated. The handle assembly 714 also includes a port 717 coupled to the vacuum 732 for generating a vacuum force at the vacuum ports 716.

Figure 28A:
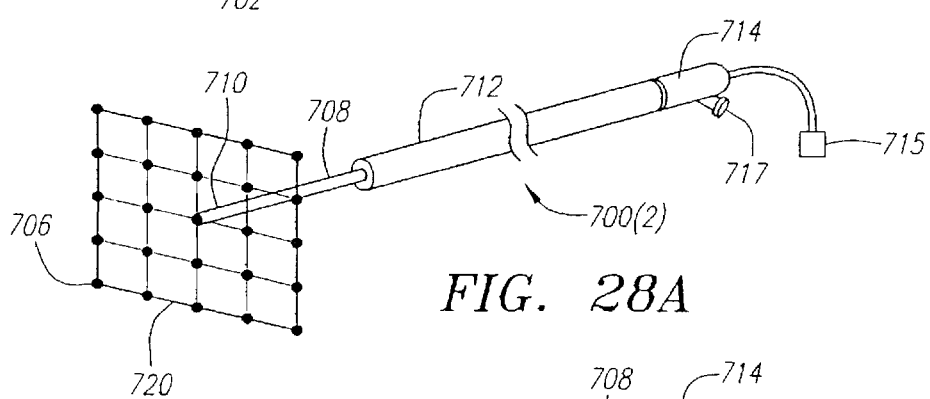
FIG. 28A is a perspective view of another embodiment of a mapping catheter that may be used with the system of FIG. 1.
Figure 28B:
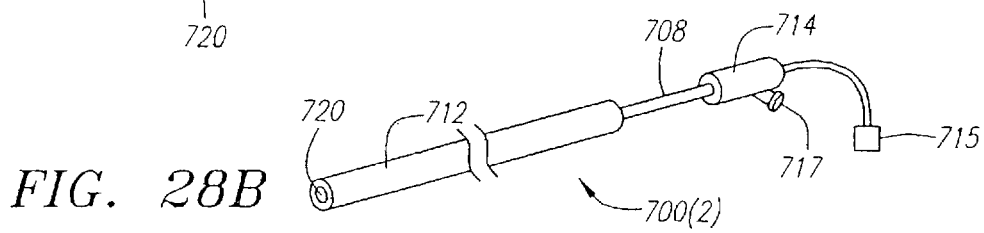
FIG. 28B is a perspective view of the mapping catheter of FIG. 28A.

FIG. 28A shows another embodiment of the mapping catheter 700(2), which is similar to the previously described embodiment. However, instead of an array 702 of spline elements 704, the mapping catheter 700(2) includes a grid or a mesh like structure 720 carrying a plurality of mapping electrodes 706. The grid 720 is preferably made from an electrically non-conductive material, such as a polymer. However, other materials may also be used for construction of the grid 720. The grid 720 assumes an expanded configuration (FIG. 28A) when it is outside the sheath 712, and assumes a collapsed configuration by proximally moving the handle 714 relative to the sheath 712, thereby retracting the grid 720 into the lumen of the sheath 712 (FIG. 28B). Although not shown, the mapping catheter 700(2), like the previously described mapping catheter 700(1), may also include stabilizing functionality.

Figure 29A:
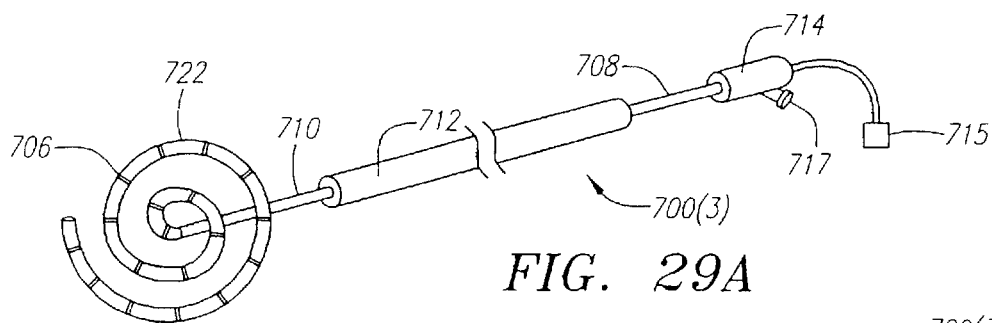
FIG. 29A is a perspective view of another embodiment of a mapping catheter that may be used with the system of FIG. 1.
Figure 29B:
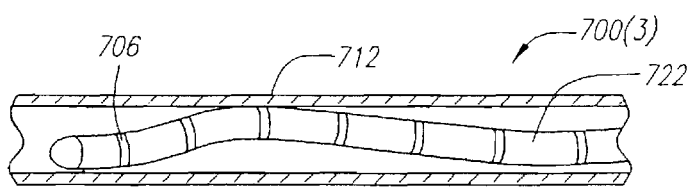
FIG. 29B is a perspective view of the mapping catheter of FIG. 29A.

FIG. 29A shows another embodiment of a mapping catheter 700(3), which includes a linear structure 722 carrying a plurality of mapping electrodes 706. The structure 722 is preferably made from an electrically non-conductive material, such as a polymer. However, other materials may also be used for construction of the structure 722. The structure 722 assumes the spiral expanded configuration when it is outside the sheath 712 (FIG. 29A), and assumes a collapsed configuration by proximally moving the handle 714 relative to the sheath 712, thereby retracting the structure 722 into the lumen of the sheath 712 (FIG. 29B). Although not shown, the mapping catheter 700(3), like the previously described mapping catheter 700(1), may also include stabilizing functionality.

Method of Use

Refer to FIGS. 30A-30D, a method of using the system 100 will now be described with reference to cardiac ablation therapy. Particularly, the method will be described with reference to the embodiment of the cannula 201 shown in FIG. 2, the embodiment of the ablation catheter 104(1) shown in FIG. 3, the embodiment of the ground catheter 106(2) shown in FIG. 24, and the embodiment of the mapping catheter 700(1) shown in FIG. 27. However, it should be understood by those skilled in the art that similar methods described herein may also apply to other embodiments of the system 100 previously described, or even embodiments not described herein.

When using the system 100 for cardiac ablation therapy, a physician initially makes an incision through a patient's skin 800 to form an opening 801. For example, a small incision or port in the intercostals space or subxiphoid may be created by a trocar (not shown). Next, the cannula 201 is inserted through the opening 801 (FIG. 30A) to reach the pericardial space of the chest cavity. The cannula 201 is distally advanced into the patient's body until the stopper 224 bear against the patient's skin 800 or against a trocar (not shown). If the position of the stopper 224 is adjustable, such as that shown in FIG. 2A, the position of the stopper 224 may be adjusted before and/or after the cannula 201 is inserted into the opening 801. The imaging device 214 and the light source 220 may be used to monitor the distance between the distal tip of the cannula 201 and the heart 802 as the cannula 201 is distally advanced into the body. Other procedures, such as a Minimally Invasive Direct Coronary Artery Bypass (MIDCAB) procedure, a conventional thoracotomy, ministernotomy, or thorascopic technique, may also be used to access the heart 802.

Figure 30A:
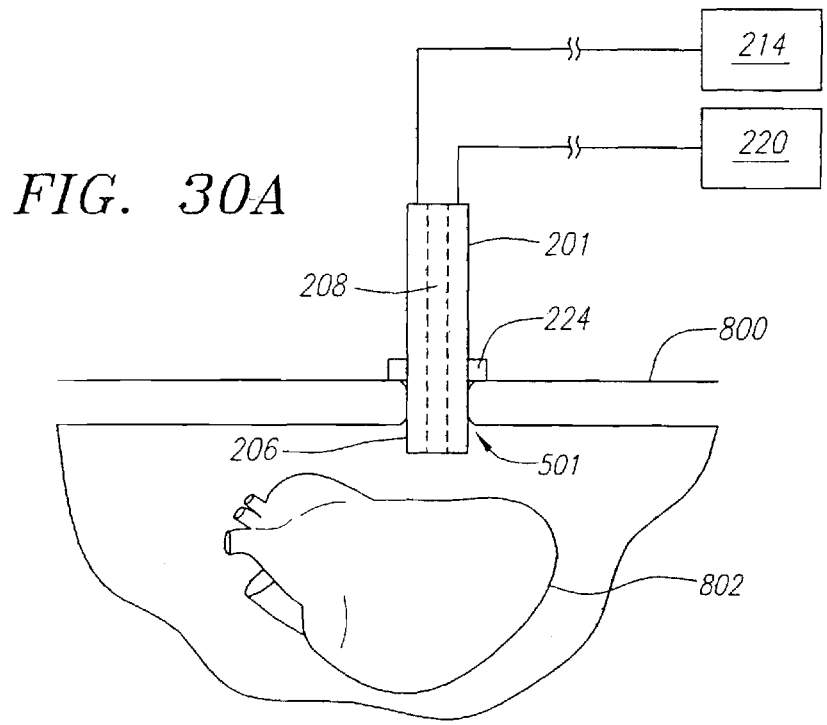
FIGS. 30A-30D are diagrams showing a method of using the system of FIG. 1 to create a transmural lesion at the right ventricle of a heart.
Figure 30B:
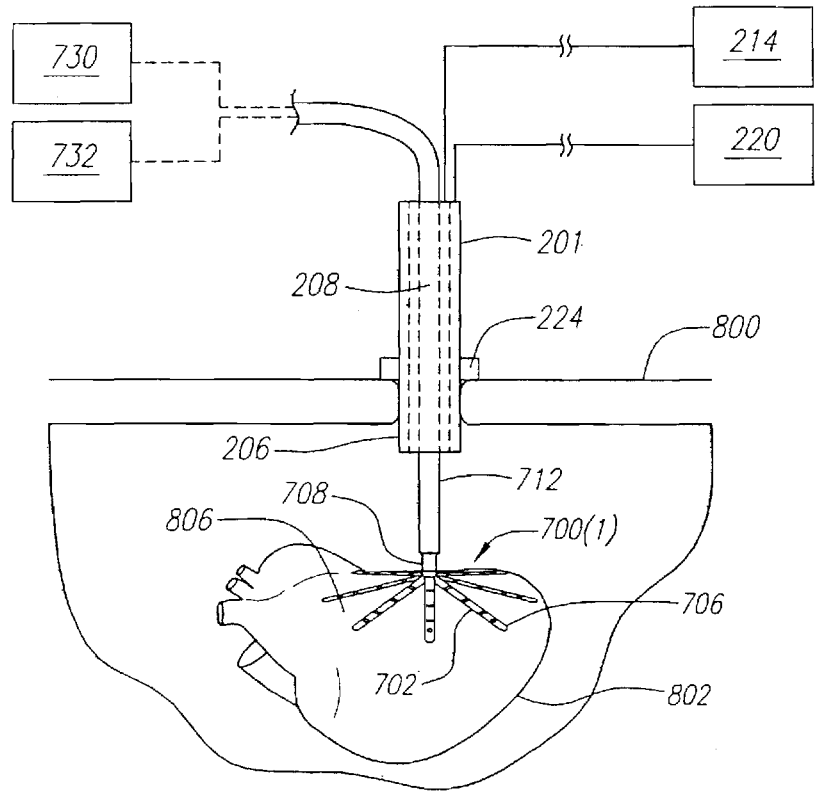

Next, the physician determines a location of a target tissue on the heart 802 to be ablated. Particularly, the mapping catheter 700(1) is employed to sense electrical signals at the heart 802, and determine a target tissue to be ablated, e.g., the region responsible for VT. To this end, the mapping catheter 700(1) is inserted into the lumen 208 of the cannula 201 and distally advanced until it exits from the distal end 206 of the cannula 201. As shown in FIG. 30B, the mapping catheter 700(1) is deployed, such that the mapping electrodes 706 are in contact with the epicardial surface 806 of the heart 802. The vacuum 732 is activated to create a vacuum within the ports 716, thereby forcing the epicardial surface 806 towards the spline elements 704 of the mapping catheter 700(1) and maintaining the cardiac tissue substantially in place relative to the array structure 702. Thus, relative movement between the mapping electrodes 706 and the epicardial surface 806 of the heart 802 is prevented, or at least minimized.

In the illustrated method, the mapping catheter 700(1) is configured to sense electrical signals at an exterior surface of the heart 802. Performing signal sensing on the exterior of the heart 802 is beneficial in that the physician can readily move the mapping catheter 700(1) around the heart 802 to obtain data at different locations on the heart 802. Once a target site is determined, it can then be marked with a biocompatible surgical ink, which can be visualized by a conventional imaging device. For example, surgical ink can be delivered through an orifice of a catheter to mark the target site. Performing signal sensing on the exterior of the heart 802 also reduces the risk of blocking a blood vessel and/or puncturing a vessel associated with mapping procedures that require a catheter steered through vessels. Alternatively, instead of performing signal sensing on the exterior of the heart 802, a suitable mapping catheter may be inserted through a vein or artery, steered to an interior of the heart 802, and be used to map electrical signals from within the heart 802 using a conventional method. In an alternative embodiment, the determination of the location of the target tissue is determined using a conventional method in a separate procedure before the operation.

For the purpose of the following discussion, it will be assumed that the target area to be ablated has been determined in the mapping session to be at the right ventricle of the heart 802. However, it should be understood that the method described herein is also applicable for performing ablation at other areas of the heart 802.

Figure 30C:
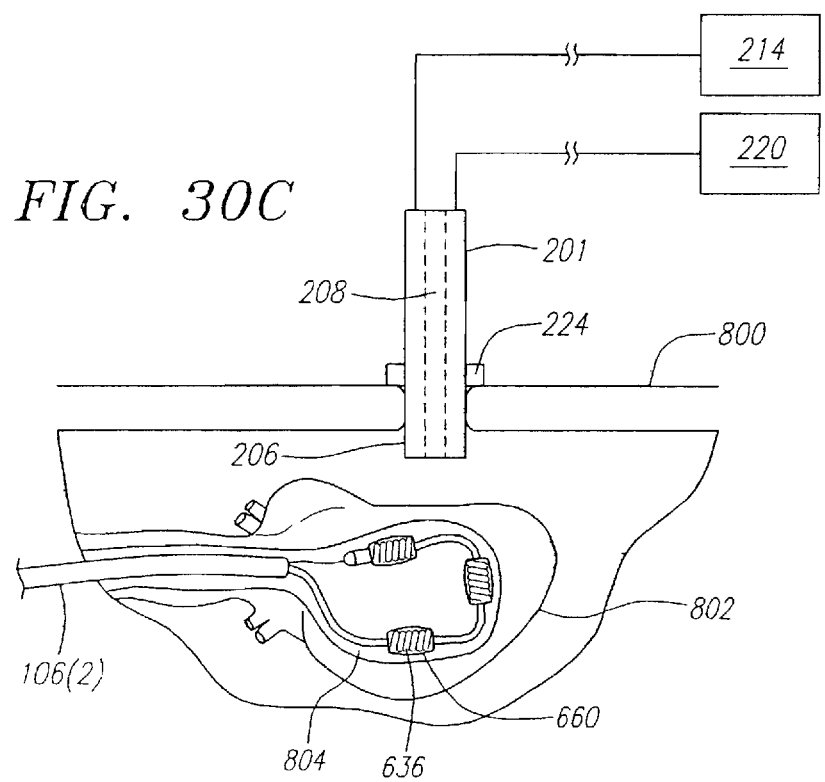

Prior to ablation, the distal end of the ground catheter 106(2) is inserted through a main vein or artery (typically the femoral vein or artery), and is steered into an interior region 804, particularly, the right ventricular chamber, of the heart (FIG. 30C). The ground catheter 106(2) can be steered by manipulating the handle assembly 608 and/or operating the steering mechanism 612 on the handle 608. Because the right ventricular chamber has a relatively wide space, the distal end of the ground catheter 106 can be bent or folded into a more voluminous configuration as described previously with reference to FIG. 25.

Figure 30D:
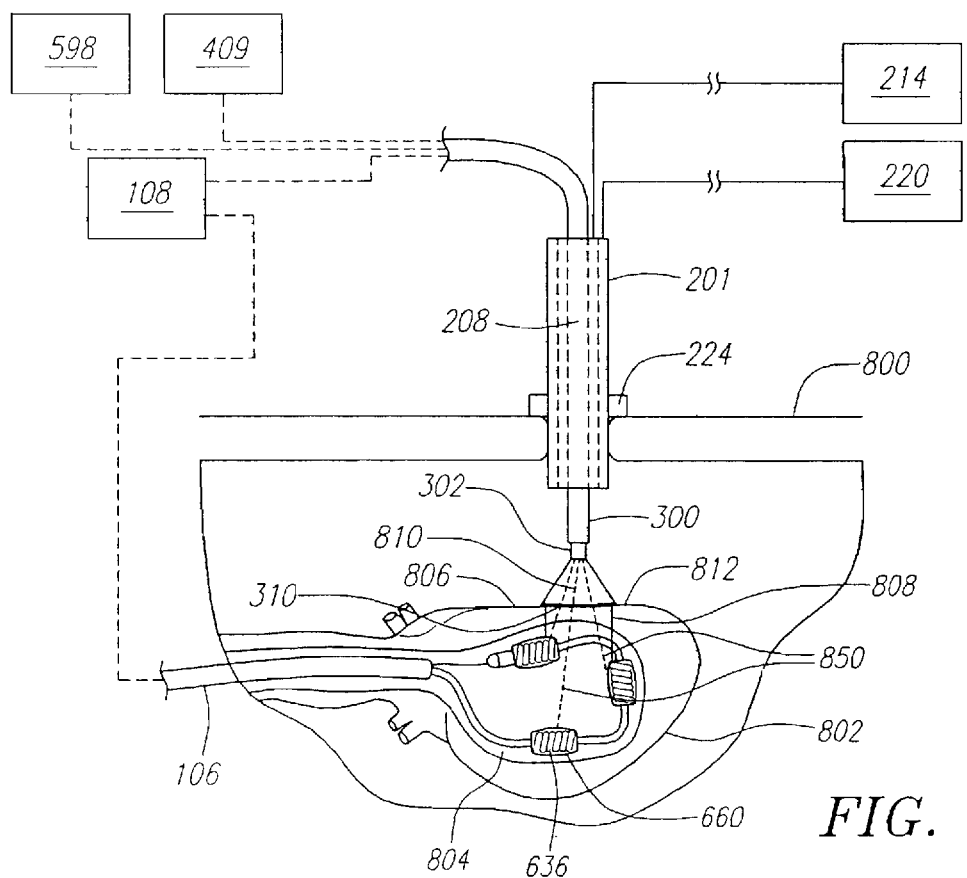

Next, the mapping catheter 700(1) is removed from the lumen 208 of the cannula 201. The distal end of the ablation catheter 104(1) is then inserted into the lumen 208 of the cannula 201, and distally advanced until it is adjacent the epicardial surface 806 of the heart 802 (FIG. 30D). Alternatively, if the cannula 201 has a dual lumen, such as that shown in FIG. 2C, the catheter 104(1) may be inserted into a second lumen of the cannula 201 while the mapping catheter 700(1) remains in the other lumen of the cannula 201, thereby avoiding the need to remove the mapping catheter 700(1). As shown in FIG. 30D, the electrode elements 636 of the ground catheter 106(2) are preferably placed in a body cavity that is next to and on one side 810 of the target tissue while the ablation catheter 104(1) is placed on the opposite side 812 of the target tissue. Particularly, the ablation catheter 104(1) is positioned adjacent a surface of the heart while the ground catheter 106 is positioned within the right ventricular chamber, such that a line 850 connecting the electrode structure 310 and the electrode elements 636 penetrates a thickness of the target tissue. The physician can further manipulate the ablation catheter 104(1) to place the electrode structure 310 in close proximity to the epicardial surface 806 of the heart that is targeted for ablation. For example, the physician may operate the steering lever 502 on the handle assembly 320 to steer the electrode structure 310, or move (i.e., torque or axially position) the handle assembly 320, for positioning the electrode structure 310. In the illustrated embodiment, the electrode structure 310 is positioned at the anterior of the heart 802 for ablation of a target area in the right ventricle. Alternatively, for ablation of other areas in the heart, the electrode structure 310 may be steered to other regions of the heart 802, such as the posterior of the heart 802.

The electrode structure 310 of the ablation catheter 104(1) is confined within the lumen of the sheath 300 as the ablation catheter 104(1) is distally advanced into the cardiac space. After the distal end of the ablation catheter 104(1) exits from the distal end 206 of the cannula 201, the sheath 300 is proximally retracted relative to the catheter member 302 until the electrode structure 310 exits from the distal end of the sheath 300. Alternatively, if the ablation catheter 104(1) does not include the sheath 300, the physician may use the lumen 208 of the cannula 201 to confine the electrode structure 310 as it is advanced through the cannula 201.

Medium 338 is then delivered from the pump 409 that is coupled to the inlet port 336 on the handle assembly 320, to the interior 334 of the expandable-collapsible body 330 to inflate the body 330. Inflation of the body 330 will cause the stabilizer 400(1) to change from its collapsed configuration to an expanded configuration.

After the body 330 is inflated, the electrode structure 310 is further distally advanced such that the distal portion of the body 330 and the stabilizer 400(1) is in contact with the epicardial surface 806 of the heart 802 at the target tissue. The vacuum 598 is activated to create a vacuum within the ports 407 of the stabilizer 400(1), thereby forcing body 330 of the ablation catheter 104(1) towards the epicardial surface 806 and maintaining the cardiac tissue substantially in place relative to the body 330. Thus, relative movement between the electrode structure 310(1) and the epicardial surface 806 of the heart 802 is prevented, or at least minimized.

Next, with the ablation catheter 104(1) coupled to the output port of the RF generator 108, and the ground catheter 106(2) coupled to the return/ground port of the RF generator 108, ablation energy is delivered from the generator 108 to the electrode structure 310 of the ablation catheter 104(1). If the electrode structure 310 includes the expandable porous body 330 with the internal electrode 350 (see FIGS. 4-10), RF energy is delivered from the generator 108 to the electrode 350 via the RF wire 360. Electric current is transmitted from the electrode 350 to the ions within the medium 338 within the body 330. The ions within the medium 338 convey RF energy through the pores 370 into the target tissue, and to the electrode elements 636 on the ground catheter 106. If the electrode structure 310 includes the expandable body 330 with the conducting shell 380 (see FIGS. 11A-11C), RF energy is delivered from the generator to the conducting shell 380 via the RF wire 381. In this case, the conducting shell 380 directly transmits the RF energy to the target tissue.

By placing the ground catheter 106(2) within the heart 802, the path of the current delivered by the electrode structure 310 is shorter, i.e., RF energy is directed from the electrode structure 310, across the target tissue, and to the electrode elements 636 of the ground catheter 106(2), thereby efficiently forming a transmural lesion 808 at the target tissue. Such configuration also allows the target tissue to be ablated without a significant dissipation of RF energy to adjacent tissues.

During the ablation process, the electrode 350 or the body 330 delivering ablation energy may overheat, thereby causing tissue charring and preventing formation of a deeper lesion.

This may negatively affect the ablation catheter's ability to create a desirable lesion. In the illustrated embodiment, the inflation medium 338 used to inflate the body 330 may be used to cool the internal electrode 350. Alternatively, an ablation catheter having active cooling capability, such as the catheter 104(3) described previously with reference to FIG. 19A, may be used. The use of active cooling in association with the transmission of DC or radio frequency ablation energy is known to force the electrode-tissue interface to lower temperature values. As a result, the hottest tissue temperature region is shifted deeper into the tissue, which in turn, shifts the boundary of the tissue rendered nonviable by ablation deeper into the tissue. An electrode that is actively cooled can be used to transmit more ablation energy into the tissue, compared to the same electrode that is not actively cooled.

During the ablation process, the electrode elements 636 may also heat up. However, the cage assemblies 660 of the ground catheter 106(2) prevents the electrode elements 636 from directly touching the healthy tissue, thereby preventing ablation of adjacent healthy tissue.

After a desired lesion 808 at the right ventricle on the heart 802 has been created, the medium 338 within the body 330 is discharged to deflate the body 330. The ablation catheter 104(1) and the ground catheter 106(2) are then retracted and removed from the interior of the patient.

In the previously described method, the system 100 is used to ablate a target tissue in a quasi-bipolar arrangement, i.e., an ablation structure and a return electrode are placed inside a body with a configuration such that a line connecting the ablation structure and the return electrode penetrates a thickness of the target tissue. The system 100 may also be used to ablate a target tissue in other quasi-bipolar arrangements.

For example, rather than placing the ground catheter 106 in the right ventricular chamber, the ground catheter 106 can be placed in other regions of the heart. For example, the ground catheter 106 may be placed within a vein, such as a pulmonary vein, an artery, a coronary sinus, a left ventricle, an inferior vena cava, or other cavity within the heart 802. If the ground catheter 106 is placed in a narrow lumen, as in a vein, the distal end of the ground catheter 106 can be placed within the region 804 such that the profile of the ground catheter 106 approximately conforms with the contour of the lumen. For example, the distal portion of the ground catheter 106 can have a curvilinear configuration that circumscribes the pulmonary vein in the left atrium of the heart 802. Furthermore, the ground catheter 106 can be placed within a body but external to the heart, while the ablation catheter 104 is placed within the heart.

In another quasi-bipolar arrangement, both the ablation catheter 104 and the ground catheter 106 are positioned within the heart, with the ablation catheter 104 placed at the target tissue within the heart, and the ground catheter 106 placed at another position adjacent the target tissue, such that a line connecting between the electrode structure carried on the ablation catheter 104 and an electrode element carried on the ground catheter 106 penetrates through a thickness of the target tissue. For example, the system 100 described previously can be used to create lesions inside the left atrium between the pulmonary veins and the mitral valve annulus. Tissue nearby these anatomic structures are recognized to develop arrhythmia substrates causing atrial fibrillation. Lesions in these tissue regions block reentry paths or destroy active pacemaker sites, and thereby prevent the arrhythmia from occurring.

For example, FIG. 31 shows (from outside the heart H) the location of major anatomic landmarks for lesion formation in the left atrium. The landmarks include the right inferior pulmonary vein (RIPV), the right superior pulmonary vein (RSPV), the left superior pulmonary vein (LSPV), the left inferior pulmonary vein (LIPV); and the mitral valve annulus (MVA). FIGS. 32A and 32B show examples of lesion patterns formed inside the left atrium based upon these landmarks.

In FIG. 32A, the lesion pattern comprises a first leg L1 between the right inferior pulmonary vein (RIPV) and the right superior pulmonary vein (RSPV); a second leg L2 between the RSPV and the left superior pulmonary vein (LSPV); a third leg L3 between the left superior pulmonary vein (LSPV) and the left inferior pulmonary vein (LIPV); and a fourth leg L4 leading between the LIPV and the mitral valve annulus (MVA). The first, second, and third legs L1-L3 can be created in a quasi-bipolar manner by directing ablation energy to the ablation catheter 104 that is placed at the left atrium (LA), while the ground catheter 106 is placed inside the left ventrical (LV), the right ventrical (RV), or the coronary sinus (CS). The fourth leg L4 can be created by directing ablation energy to the ablation catheter 104 that is placed at the LA, while the ground catheter 106 is placed inside the CS. In alternative methods, the positions of the ablation catheter 104 and the ground catheter 106 described previously may be exchanged.

FIG. 32B shows a criss-crossing lesion pattern comprising a first leg L1 extending between the RSPV and LIPV; a second leg L2 extending between the LSPV and RIPV; and a third leg L3 extending from the LIPV to the MVA. The first and second legs L1, L2 can be created by directing ablation energy to the ablation catheter 104 placed at the LA, while the ground catheter 106 is placed inside the LV, RV, or the CS. The third leg L3 can be created by directing ablation energy to the ablation catheter 104 placed at the LA, while the ground catheter 106 is placed inside the CS. In alternative embodiments, the positions of the ablation catheter 104 and the ground catheter 106 described previously may be exchanged.

The system 100 described previously can also be used to create lesions inside the right atrium. FIG. 31 shows (from outside the heart H) the location of the major anatomic landmarks for lesion formation in the right atrium. These landmarks include the superior vena cava (SVC), the tricuspid valve annulus (TVA), the inferior vena cava (IVC), and the coronary sinus (CS). Tissue nearby these anatomic structures have been identified as developing arrhythmia substrates causing atrial fibrillation. Lesions in these tissue regions block reentry paths or destroy active pacemaker sites and thereby prevent the arrhythmia from occurring.

FIGS. 33A to 33C show representative lesion patterns formed inside the right atrium based upon these landmarks. FIG. 33A shows a representative lesion pattern L that extends between the superior vena cava (SVC) and the tricuspid valve annulus (TVA). The lesion L can be created in a quasi-bipolar manner by directing ablation energy to the ablation catheter 104 placed at the LA, while the ground catheter 106 is placed inside the LV or the RV. In an alternative embodiment, the positions of the ablation catheter 104 and the ground catheter 106 may be exchanged.

FIG. 33B shows a representative lesion pattern that extends between the interior vena cava (IVC) and the TVA. The lesion L can be created in a quasi-bipolar manner by directing ablation energy to the ablation catheter 104 placed at the LA, while the ground catheter 106 is placed inside the LV or the RV. In an alternative embodiment, the positions of the ablation catheter 104 and the ground catheter 106 may be exchanged.

FIG. 33C shows a representative lesion pattern L that extends between the coronary sinus (CS) and the tricuspid valve annulus (TVA). The lesion L can be created by directing ablation energy to the ablation catheter 104 placed at the right atrium (RA), while the ground catheter 106 is placed inside the LV, the RV, or the CS. In an alternative embodiment, the positions of the ablation catheter 104 and the ground catheter 106 may be exchanged.

Although several examples of lesions that can be created using the above-described system have been discussed, the above described system and method can also be used to create lesions at other locations of the heart. For example, in one embodiment, one of the ablation catheter and ground catheter 104, 106 can be placed at the atrium at the base of a heart, while the other of the ablation catheter and ground catheter 104, 106 is placed at the LV. Such placement of the ablation and ground catheters 104, 106 allows a lesion to be created at the intersection of the atria and the ventricle. In another embodiment, one of the ablation catheter and ground catheter 104, 106 can be placed at the RV next to the septum, while the other of the ablation catheter and ground catheter 104, 106 is placed at the LV. Such placement of the ablation and ground catheters 104, 106 allows a lesion to be created at the ventricular septum. In addition, although the above described system and method have been described in the context of cardiac ablation therapy, e.g., for treating arrhythmias, such as ventricular tachycardia (VT), post-myocardial infraction, atrial fibrillation, supra-VT, flutter, and other heart conditions, it should be understood that the system 100 may also be used in many different environments and/or applications. For example, the system 100 may also be used to create lesions, such as transmural lesions, at different locations within the body.

Thus, although different embodiments have been shown and described, it would be apparent to those skilled in the art that many changes and modifications may be made thereunto without the departing from the scope of the invention, which is defined by the following claims and their equivalents.

What is claimed is:

1. A medical probe, comprising:
   an elongate member having a proximal end and a distal end;
   an operative element mounted to the distal end of the elongate member, the operative element configured for conveying or returning ablation energy;
   an expandable-collapsible body surrounding the operative element, wherein the expandable-collapsible body surrounds the operative element to prevent the operative element from contacting solid tissue, and wherein the expandable-collapsible body is inflatable and allows the transport of ablation energy from the operative element to outside the expandable-collapsible body; and
   an actuatable stabilizer mounted to the distal end of the elongate member, the stabilizer extending along at least a portion of an exterior surface of the expandable-collapsible body when the expandable-collapsible body is in both an expanded configuration and a collapsed configuration.

2. The medical probe of claim 1 wherein the elongate member comprises an inflation lumen having a distal port distal the distal end of the elongate member.

3. The medical probe of claim 2 wherein the elongate member comprises a vacuum lumen having a distal port distal the distal end of the elongate member.

4. The medical probe of claim 3 wherein the inflation lumen distal port is longitudinally spaced from the vacuum lumen distal port.

5. The medical probe of claim 2 wherein the inflation lumen distal port is distal the operative element.

6. The medical probe of claim 2 wherein the inflation lumen extends through the operative element.

7. The medical probe of claim 1 wherein the expandable-collapsible body comprises a first layer made from a non-electrically conductive material.

8. The medical probe of claim 7 wherein the pores have a diameter of about 0.1 micrometers.

9. The medical probe of claim 8, wherein the expandable-collapsible body comprises a second layer, the second layer being an electrically conductive layer.

10. The medical probe of claim 9, wherein the expandable-collapsible body has an outer surface and the outer surface has an area, and wherein the electrically conductive layer has an exposed area of an outwardly facing surface, and wherein the exposed area of the outwardly facing surface of the electrically conductive layer is less than the area of the outer surface of the expandable-collapsible body.

11. The medical probe of claim 1, wherein the expandable-collapsible body comprises pores in the first layer.

12. The medical probe of claim 11, wherein the inflation lumen distal port faces towards at least some of the pores.

13. The medical probe of claim 1, further comprising a handle assembly secured to a proximal end of the elongate member.

14. The medical probe of claim 13, wherein the handle assembly comprises a steering mechanism.

15. The medical probe of claim 1, wherein the operative element is an electrode element configured to provide radiofrequency energy.

16. The medical probe of claim 15, wherein the electrode element surrounds the inflation lumen.

17. The medical probe of claim 1, wherein the expandable-collapsible body circumscribes the operative element.

18. A method of treating solid tissue in a body using the medical probe of claim 1, comprising:
   inserting the elongate member into the body to place the operative element;
   placing the operative element adjacent the solid tissue; and
   maintaining a distance between the operative element and the solid tissue using the operative element.

19. The method of claim 18, further comprising conveying energy between the operative element and the solid tissue, wherein the solid tissue is not ablated by the operative element.

20. The medical probe of claim 1, wherein the stabilizer circumscribes at least a portion of the exterior surface of the expandable-collapsible body.

21. The medical probe of claim 1, wherein the stabilizer comprises a material having low electrical conductivity.

22. The medical probe of claim 1, wherein the stabilizer is vacuum actuatable.

* * * * *